US010213782B2

(12) United States Patent
Bailey et al.

(10) Patent No.: US 10,213,782 B2
(45) Date of Patent: Feb. 26, 2019

(54) MICROFLUIDIC DEVICES

(71) Applicant: The Board of Trustees of the University of Illinois, Urbana, IL (US)

(72) Inventors: Ryan C. Bailey, Urbana, IL (US); Steven R. Doonan, Urbana, IL (US); Yi Xu, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 314 days.

(21) Appl. No.: 15/059,098

(22) Filed: Mar. 2, 2016

(65) Prior Publication Data
US 2016/0258902 A1  Sep. 8, 2016

Related U.S. Application Data

(60) Provisional application No. 62/127,679, filed on Mar. 3, 2015.

(51) Int. Cl.
*G01N 27/447* (2006.01)
*B01L 3/00* (2006.01)
*B01L 3/02* (2006.01)

(52) U.S. Cl.
CPC ....... *B01L 3/502784* (2013.01); *B01L 3/0241* (2013.01); *B01L 3/502715* (2013.01); *B01L 2200/0668* (2013.01); *B01L 2200/0673* (2013.01); *B01L 2300/0645* (2013.01); *B01L 2300/0864* (2013.01);
(Continued)

(58) Field of Classification Search
CPC ......... G01N 27/44791; B01L 3/502715; B01L 3/502784; B01L 3/502
See application file for complete search history.

(56) References Cited

U.S. PATENT DOCUMENTS 6,500,323 B1* 12/2002 Chow .................. B01L 3/5027
  204/450
2010/0224493 A1* 9/2010 Davalos ................ B03C 5/005
  204/547

(Continued)

OTHER PUBLICATIONS

Fallah-Araghi et al., A completely in vitro ultrahigh-throughput droplet-based microfluidic screening system for protein engineering and directed evolution, Lab Chip, 2012, 12, 882-891 (DOI: 10.1039/C2LC21035E).
(Continued)

*Primary Examiner* — Alexander S Noguerola
(74) *Attorney, Agent, or Firm* — Klarquist Sparkman, LLP

(57) ABSTRACT

In one representative embodiment, a device includes a main microchannel and at least two other microchannels. The main microchannel defines a main fluid flow path and has an opening, and first and second microchannels defining a first and second fluid flow paths, respectively. The first fluid flow path is in fluidic communication with the main fluid flow path via the opening and forms a first angle relative to the main microchannel less than 90 degrees. The second microchannel defines a second fluid flow path in fluidic communication with the main fluid flow path via the opening and in fluidic communication with the first fluid flow path. The second microchannel forms a second angle relative to the main microchannel less than 90 degrees. The first and second microchannels form a third angle relative to one another, with the third angle being between 60 and 135 degrees.

19 Claims, 25 Drawing Sheets

(52) U.S. Cl.
CPC ............... *B01L 2300/0867* (2013.01); *B01L 2300/0883* (2013.01); *B01L 2400/043* (2013.01); *B01L 2400/0415* (2013.01); *G01N 27/44791* (2013.01)

(56) References Cited

U.S. PATENT DOCUMENTS

2012/0091004 A1* 4/2012 Abell ............... B01J 19/0093
204/556
2013/0028812 A1* 1/2013 Prieto ............ B01L 3/502784
422/502

OTHER PUBLICATIONS

Lin et al., Novel on-demand droplet generation for selective fluid sample extraction, Amer. Institute of Physics, *Biomicrofluidics* 6, Jun. 2012, 024103-01 to 024103-10, (available at http://dx.doi.org/10.1063/1.3699972).

\* cited by examiner

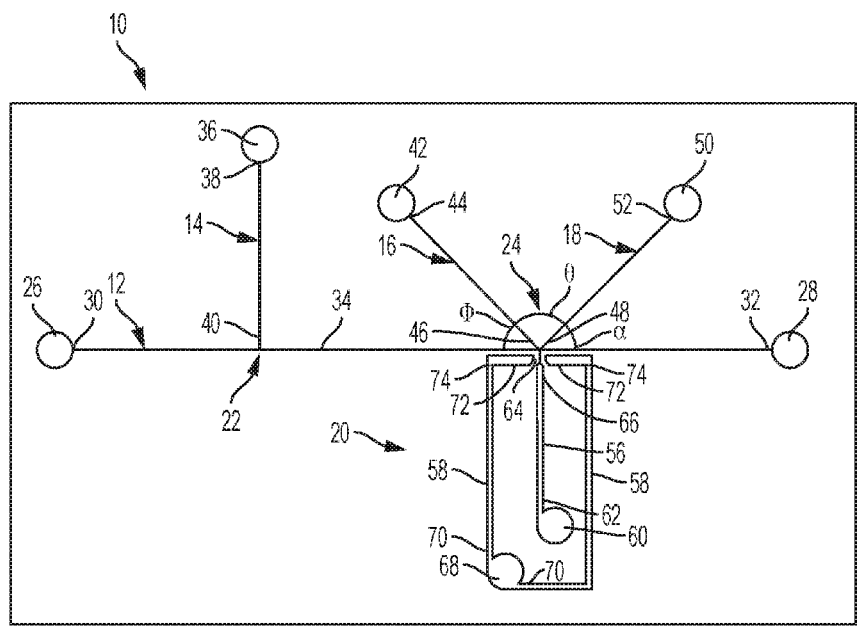
FIG. 1A
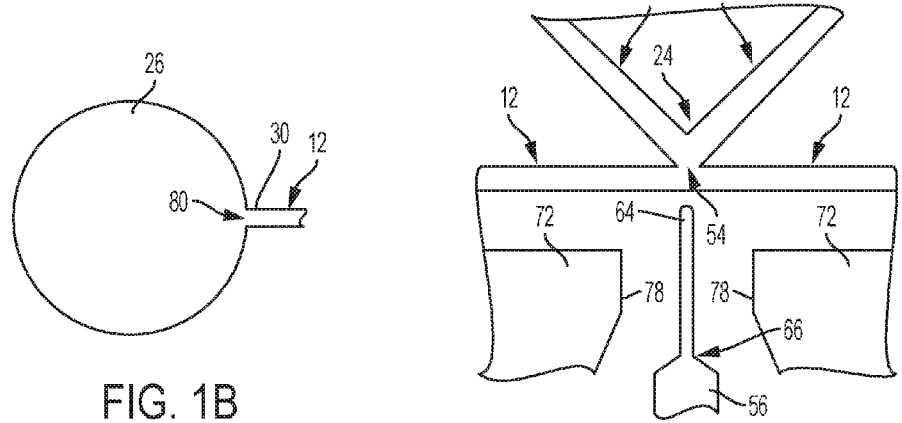
FIG. 1B
FIG. 1C

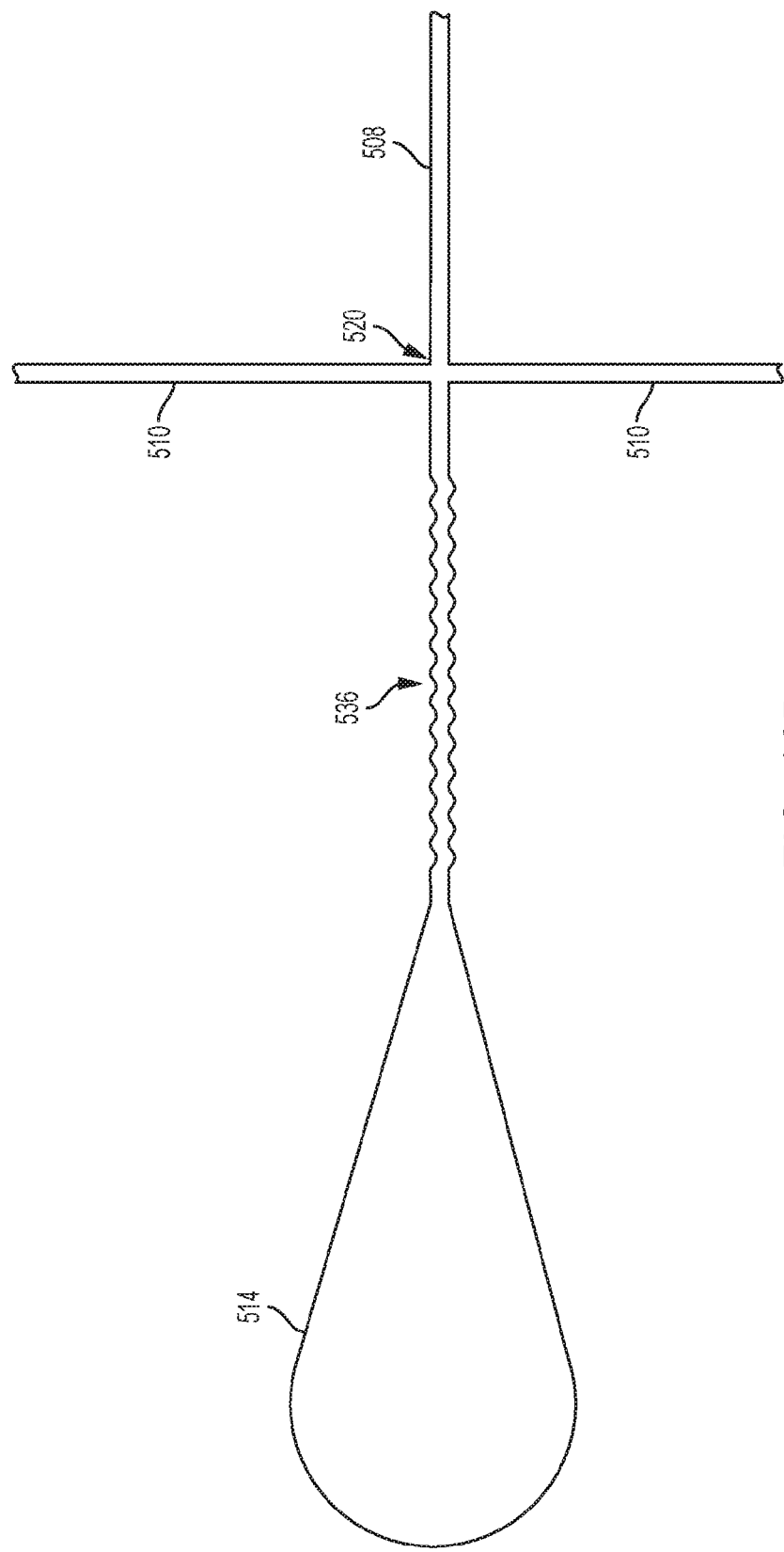

MICROFLUIDIC DEVICES

CROSS REFERENCE TO RELATED APPLICATION

This application claims the benefit of U.S. Provisional Application Ser. No. 62/127,679, entitled MICROFLUIDIC DEVICES, filed on Mar. 3, 2015, which is incorporated by reference herein.

FIELD

The present disclosure generally concerns microfluidic devices and related methods for using such devices.

BACKGROUND

Microfluidics involve the control and manipulation of fluids at a small scale. Using microfluidics, fluids can be moved, mixed, separated, or otherwise processed. One particularly popular area of microfluidics is droplet microfluidics, which involves manipulating discrete volumes of fluids. Systems that use droplet-based microfluidics include, for example, fast analytical systems or the synthesis of advanced materials to protein crystallization and biological assays for living cells. Conventional droplet generation and manipulation devices and methods, however, suffer from various shortcomings. Accordingly, there is a continuing need from improved devices and methods for generating and manipulating droplets.

SUMMARY

Described herein are embodiments of microfluidic devices that are primarily intended to be used for the creation and/or manipulation of droplets in droplet-based microfluidic systems, as well as systems and methods for using the same. The microfluidic devices can be used to generate droplets, extract or inject volume to droplets, and/or split droplets. The microfluidic devices can also be used to alter droplet spacing. The disclosed devices can comprise electrode channels for droplet destabilization and manipulation.

In one embodiment, a device includes a main microchannel and at least two other microchannels. The main microchannel defines a main fluid flow path and has an opening, and first and second microchannels defining a first and second fluid flow paths, respectively. The first fluid flow path is in fluidic communication with the main fluid flow path via the opening and forms a first angle relative to the main microchannel less than 90 degrees. The second microchannel defines a second fluid flow path in fluidic communication with the main fluid flow path via the opening and in fluidic communication with the first fluid flow path. The second microchannel forms a second angle relative to the main microchannel less than 90 degrees. The first and second microchannels form a third angle relative to one another, with the third angle being between 60 and 135 degrees.

In some embodiments, the device includes one or more fluid control members to alter fluid flow and/or pressure in the flow paths. A main fluid control member can be configured to control the flow of a first fluid in the main fluid flow path and at least one additional fluid control member configured to control the flow of a second fluid in the first and second fluid flow paths. In some embodiments, the first fluid is delivered along the main fluid flow path in a first direction and second fluid is delivered along the side flow path in a second direction, and at the opening the second direction is generally parallel to the first direction. In other embodiments, the first fluid is delivered along the main fluid flow path in a first direction and second fluid is delivered along the side flow path in a second direction, and at the opening the second direction is generally opposite of the first direction. In other embodiments, an electric field generator having one or more microchannels positioned adjacent the main fluid flow path at the location of the opening.

In some embodiments, the main fluid control member and the at least one additional fluid control member are configured to form droplets in the main flow path at the opening. In some embodiments, the main fluid control member and the at least one additional fluid control member are configured to alter spacing of droplets in the main flow path at the opening.

In other embodiments, a method for manipulating droplets in microfluidics system is provided. The method can include delivering a plurality of droplets and a first fluid through a main fluid flow path of a main microchannel and delivering a second fluid through along a side flow path defined by intersecting first and second microchannels. The first and second microchannels can form an angle therebetween and intersect with one another at an opening in the main microchannel. The method can include altering a volume of one or more of the plurality of droplets as respective droplets move along the main fluid flow path and pass the opening in the main microchannel.

In some embodiments, the act of altering the volume of the one or more of the plurality of droplets comprises removing a portion of the one or more droplets and directing the removed portion into the side flow path, and/or increasing the volume of the one or more droplets by injecting a fluid from the side flow path into the main fluid flow path. The relative directions of fluid in the main fluid flow path and the side flow path can vary. The first fluid can be delivered along the main fluid flow path in a first direction and second fluid is delivered along the side flow path in a second direction. At the intersection of the first and second microchannels the second direction can be generally parallel to the first direction or it can be opposite. In some embodiments, the method can include applying an electric field to the plurality of droplets adjacent to the opening in the main microchannel.

In other embodiments, another method for manipulating droplets in microfluidics system is provided. The method can include delivering a plurality of droplets and a first fluid along a main fluid flow path of a main microchannel, delivering a second fluid along a side flow path defined by a side microchannel, the side microchannel intersecting with the main microchannel at an opening in the main microchannel, applying an electric field to the plurality of droplets at the opening in the main microchannel by aligning a first electrode and a second electrode relative to each other and positioning the first and the second electrodes adjacent to the opening in the main microchannel, and extracting one or more of the plurality of droplets into the side microchannel as respective droplets move along the main fluid flow path and pass the opening in the main microchannel.

In another embodiment, a device includes a main microchannel defining a main fluid flow path and having an opening, a first microchannel defining a first fluid flow path, the first fluid flow path being in fluidic communication with the main fluid flow path via the opening, and an electric field generator having a first electrode and a second electrode which are aligned relative to each other and disposed adjacent to the opening.

The foregoing and other objects, features, and advantages of the invention will become more apparent from the following detailed description, which proceeds with reference to the accompanying figures.

BRIEF DESCRIPTION OF THE DRAWINGS

FIG. 1A is a schematic of a microfluidic device, according to one embodiment.

FIGS. 1B-1C are various detail views of the microfluidic device.

FIG. 16A-16D show a microfluidic device, according to another embodiment.

DETAILED DESCRIPTION

General Considerations

Figure 1D:
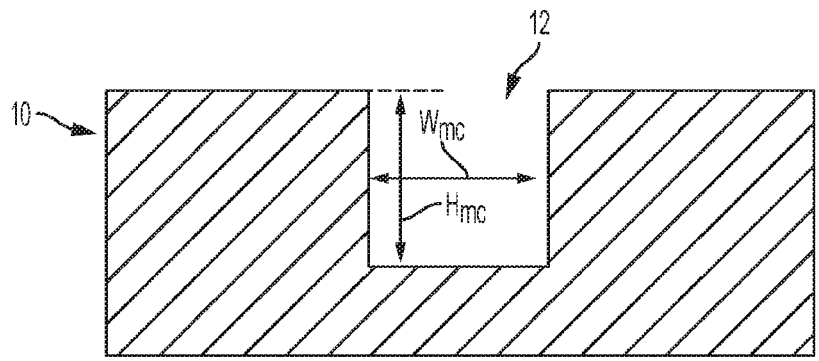
FIGS. 1D-1G are various partial cross-sectional views of the microfluidic device.

For purposes of this description, certain aspects, advantages, and novel features of the embodiments of this disclosure are described herein. The disclosed devices, methods, and systems should not be construed as limiting in any way. Instead, the present disclosure is directed toward all novel and nonobvious features and aspects of the various disclosed embodiments, alone and in various combinations and sub-combinations with one another. The devices, methods, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the "connected" generally means that joined or linked such that there is fluidic communication between the elements and does not exclude the presence of intermediate elements between connected items, absent specific contrary language.

Described herein are embodiments of microfluidic devices that are primarily intended to be used for the creation and/or manipulation of droplets in droplet-based microfluidic systems, as well as systems and methods for using the same. The microfluidic devices can be used to generate droplets, extract or inject volume to droplets, and/or split droplets. The microfluidic devices can also be used to alter droplet spacing. The disclosed embodiments should not be construed as limiting in any way. Instead, the present disclosure is directed toward all novel and nonobvious features and aspects of the various disclosed embodiments, alone and in various combinations and sub-combinations with one another.

In particular embodiments, a microfluidic device includes at least one "K-junction." As used herein, the term "K-junction" means a device or portion of a device that includes at least one main channel and at least two side channels that intersect or engage with the main channel at an angle, resulting in a shape that resembles the letter "K." In some embodiments, the K-junction can be configured to generate droplets, extract or inject volume to droplets, split droplets, alter droplet spacing, or otherwise process a fluid traveling in the main and/or side channels. This improves the functionality and versatility of the microfluidic device.

In particular embodiments, a microfluidic device includes one or more electrode channels at or near the K-junction. The electrode channels can be configured to enhance droplet destabilization and manipulation at the K-junction.

Referring first to FIG. 1A, there is shown an example of a microfluidic device 10 comprising a K-junction, according to one embodiment. The microfluidic device 10 can comprise a main channel 12, a droplet formation channel 14, a first side channel portion 16, a second side channel portion 18, and an electric field generator portion 20. The first, side channel 14 can, for example, be connected to the main channel 12 by forming a T-junction 22 between the first side channel 14 and the main channel 12, as further described below. The first and the second side channels 16, 18 can, for example, each be connected to the main channel portion 12 to each other by forming a K-junction 24 between the main channel 12 and the first and second side channels 16, 18, as further described below. The electrical field generator portion 20 can be disposed near or adjacent to the K-junction 24 formed by the main channel 12 and the first and second side channels 16, 18, as further described below.

Exemplary Description of a Main Channel

The main channel 12 can comprise a first port or opening 26 and a second port or opening 28. The first port 26 can be connected to a first end portion 30 of the main channel 12, and the second port 28 can be connected to a second end portion 32 of the main channel 12. The first and second ends 30, 32 of the main channel 12 can be separated by an intermediate portion 34 of the main channel 12. The T-junction 22 and the K-junction 24 can be spaced apart (relative to each other) and disposed on intermediate portion 34 of the main channel 12. For example, the T-junction 22 can be disposed on the intermediate portion 34 towards the first end 30, relative to the K-junction 24.

The main channel 12 can be configured with various dimensions and/or cross-sectional shapes. For example, as best shown in FIG. 1D, the main channel 12 has a generally rectangular cross-sectional shape with a height $H_{mc}$ and a width $W_{mc}$. In some embodiments, the height $H_{mc}$ can be about 10 µm to 200 µm and the width $W_{mc}$ can be about 10 µm to about 200 µm. In preferred embodiments, the height $H_{mc}$ can be about 30 µm to about 50 µm and the width $W_{mc}$ can be about 30 µm to about 50 µm. In the illustrated embodiment, for example, the height $H_{mc}$ can be about 40 µm and the width $W_{mc}$ can be about 40 µm.

The main channel 12 can also comprise a length (i.e., the distance from the first end 30 to the second end 32 of the main channel 12). The length can vary depending on the application. In the illustrated embodiment of FIG. 1A, for example, the length of the main channel 12 is about 15 mm.

Exemplary Description of a Droplet Formation Channel

The droplet formation channel 14 can comprise a third port 36 which is connected to a first end 38 of the droplet formation channel 14. A second end 40 of the droplet formation channel 14 can be connected to the main channel 12 at the T-junction 22. The droplet formation channel 14 can be configured with various dimensions and/or cross-sectional shapes, similar to the main channel 12. Although not shown, the droplet formation channel can have a generally rectangular cross-sectional shape with a height and a width. In some embodiments, the droplet formation channel 14 can, for example, have height of about 10 µm to 200 µm and a width of about 10 µm to about 200 µm. In some embodiments, the droplet formation channel 14 can, for example, have a height of about 30 µm to about 50 µm and a width of about 30 µm to about 50 µm. In the illustrated embodiment, for example, the droplet formation channel 14 has a height of about 40 µm and the width of about 40 µm.

The droplet formation channel 14 can also comprise a length (i.e., the distance from the first end 38 to the second end 40 of the droplet formation channel 14). The length can vary depending on the application. In the illustrated embodiment of FIG. 1A, for example, the length of the droplet formation channel 14 is about 4 mm.

Figure 16A:
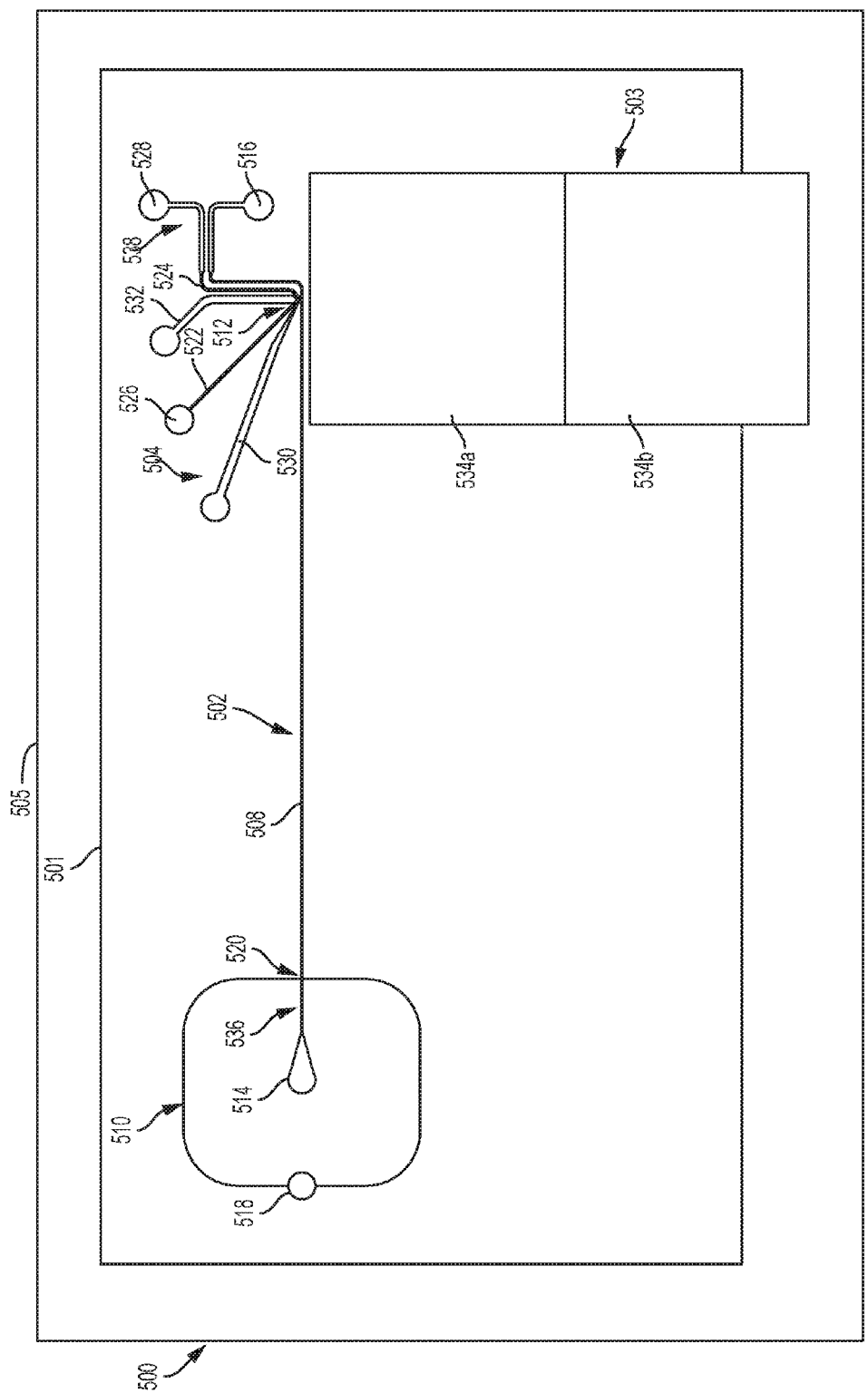

In other embodiments, a Flow Focusing junction can be used for droplet formation. Such embodiments form droplets by flowing oil from an oil inlet where it bifurcates into two streams that simultaneously merge from opposite directions with an aqueous stream from an aqueous inlet focused between the oil streams to encapsulate fluid from the aqueous stream into droplets. For example, the device 500 includes a Flow Focusing junction 520 to form droplets, as shown in FIG. 16A.

Exemplary Description of a First Side Channel

A K-junction can be formed of at least two side channels, such as first side channel 16 and second side channel 18 as shown in FIG. 1A.

The first side channel 16 can comprise a fourth port 42 which is connected to a first end 44 of the first side channel 16. A second end 46 of the first side channel 16 can be connected to the intermediate portion 34 of the main channel 12 and to a second end 48 of the second side channel 18, as best shown in FIG. 1C and further described below.

Figure 1E:
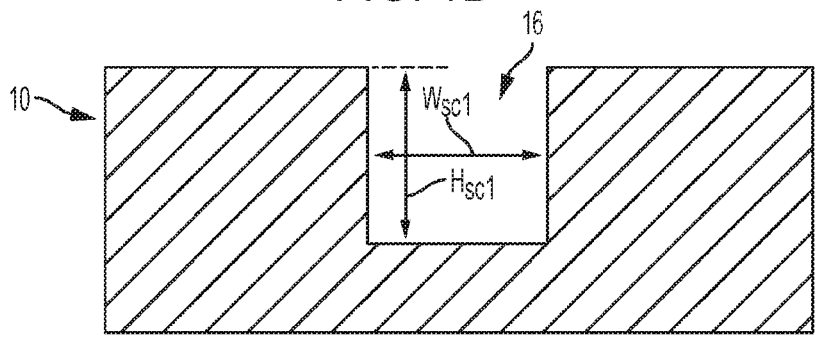

The first side channel 16 can be configured with various dimensions and/or cross-sectional shapes. For example, as best shown in FIG. 1E, the first side channel 16 has a generally rectangular cross-sectional shape with a height $H_{sc1}$ and a width $W_{sc1}$. In some embodiments, the height $H_{sc1}$ can be about 10 µm to about 200 µm and the width $W_{sc1}$ can be about 10 µm to about 200 µm. In preferred embodiments, the height $H_{sc1}$ can be about 30 µm to about 50 µm and the width $W_{sc1}$ can be about 30 µm to about 50 µm. In one particular embodiment, the height $H_{sc1}$ can be about 40 µm and the width $W_{sc1}$ can be about 40 µm. In the illustrated embodiment, for example, the height $H_{sc1}$ is about 40 µm and the width $W_{sc1}$ is about 40 µm.

The first side channel 16 can also comprise a length (i.e., the distance from the first end 44 to the second end 46 of the first side channel 16). The length can vary depending on the application. In the illustrated embodiment of FIG. 1A, the length of the first side channel 16 is about 4 mm.

Exemplary Description of a Second Side Channel

The second side channel 18 can comprise a fifth port 50 which is connected to a first end 52 of the second side channel 18. As mentioned above, the second end 48 of the second side channel 18 can be connected to the intermediate portion 34 of the main channel 12 and to a second end 46 of the first side channel 16, as best shown in FIG. 1C and further described below.

Figure 1F:
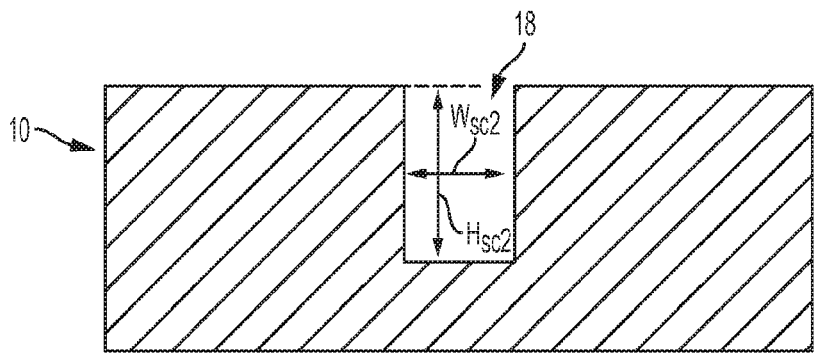

The second side channel 18 can be configured with various dimensions and/or cross-sectional shapes. For example, as best shown in FIG. 1F, the second side channel 18 has a generally rectangular cross-sectional shape with a height $H_{sc2}$ and a width $W_{sc2}$. In some embodiments, the height $H_{sc2}$ can be about 10 µm to about 200 µm and the width $W_{sc2}$ can be about 10 µm to about 200 µm. In preferred embodiments, the height $H_{sc2}$ can be about 30 µm to about 50 µm and the width $W_{sc2}$ can be about 10 µm to about 50 µm. In one particular embodiment, the height $H_{sc2}$ can be about 40 µm and the width $W_{sc2}$ can be about 40 µm. In yet another particular embodiment, the height $H_{sc2}$ can be about 40 µm and the width $W_{sc2}$ can be about 15 µm. In the illustrated embodiment, for example, the height $H_{sc2}$ is about 40 µm and the width $W_{sc2}$ is about 25 µm.

The second side channel 18 can also comprise a length (i.e., the distance from the first end 52 to the second end 48 of the first side channel 16). The length can vary depending on the application. In the illustrated embodiment of FIG. 1A, for example, the length of the second side channel 18 is about 4 mm.

At the K-junction 24, the first and second side channels 16, 18 can, for example, be connected by chamfering or beveling the second ends 46, 48 of the first and second side channels 16, 18 relative to each other such the second ends 46, 48 open into each other, as shown in the illustrated embodiment. In an alternative embodiment, the first and second channels can, for example, be connected by a radius or curved joint or connecting portion.

Figure 1G:
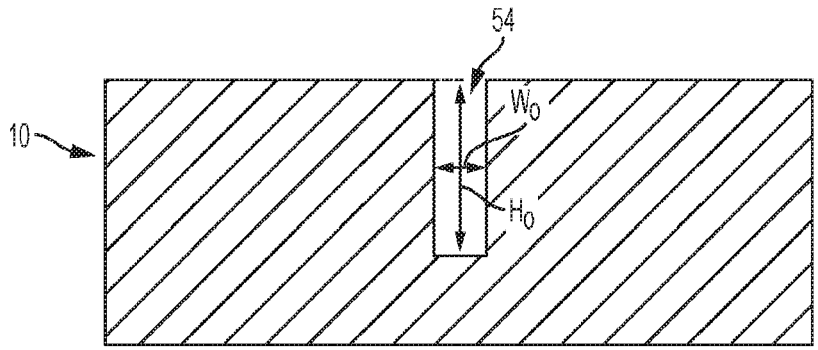

The first and second channels 16, 18 can be connected to the main channel by an opening 54, as best shown in FIG. 1C. The opening 54 can be configured with various dimensions and/or cross-sectional shapes. For example, as best shown in FIG. 1G, the opening 54 has a generally rectangular cross-sectional shape with a height $H_o$ and a width $W_o$. In some embodiments, the height $H_o$ can be about 10 µm to about 200 µm and the width $W_o$ can be about 10 µm to about 200 µm. In preferred embodiments, the height $H_o$ can be about 30 µm to about 50 µm and the width $W_o$ can be about 5 µm to about 30 µm. In the illustrated embodiment, for example, the height $H_o$ is about 40 µm and the width $W_o$ is about 10 µm.

The second side 16 can be positioned at an angle θ relative to the second side channel 18, and the first and second sides 16, 18 can be positioned at respective angles φ and α relative to the main channel 12. In some embodiments, (e.g., the illustrated embodiment) the angles φ and α can be substantially equal. Or in other words, the first channel 16 and the second channel 18 can be substantially symmetrical relative to the main channel 12. In alternative embodiments, the angles ϕ and α can be different such that the first channel 16 and the second channel 18 are asymmetrical relative to the main channel 12.

In some embodiments, the angle θ can be from about 60 degrees to about 135 degrees. In preferred embodiments, the angle θ can be from about 75 degrees to about 115 degrees. In the illustrated embodiment, for example, the angle θ is about 90 degrees. In some embodiments, the angle ϕ can be about 20 degrees to about 60. In the illustrated embodiment, for example, the angle ϕ is about 45 degrees. In some embodiments, the angle α can be about 20 degrees to about 60 degrees. In the illustrated embodiment, for example, the angle α is about 45 degrees.

The electrical field generator 20 can include at least one source channel portion 56 (one in the illustrated embodiment) and at least one ground channel portion 58 (two in the illustrated embodiment), as best shown in FIG. 1A. The source channel 56 can be connected to a sixth port 60 at a first end 62 of the source channel 56, and the source channel 56 can comprise an electrode 64 portion (FIG. 1C) at a second end 66 of the source channel 56. The ground channels 58 can each be connected to a seventh port 68 at first ends 70 of the ground channels 58, and the ground channels 58 can each comprise a respective electrode 72 portion (FIG. 1C) at second ends 74 of the ground channels 58, as best shown in FIG. 1A.

The source channel 56 and ground channel 58 can be configured with various dimensions and/or cross-sectional shapes. For example, the source channel 56 and ground channels 58 can have a generally rectangular cross-sectional shape with a height and a width, and the height of the source channel 56 is about 40 μm, and the width of the source channel 56 is about 100 μm.

The electrode portion 72 of each ground channel 58 can be spaced apart relative to each other, spanning the opening 54, and the tips 78 of the electrodes 72 can be directed substantially towards each other, as best shown in FIG. 1C. The electrode 64 of the source channel 56 can be spaced apart from and disposed between the tips 78 of the electrodes 72 of the ground channels 58. The electrode 64 of the source channel 56 can be spaced apart from and disposed near or adjacent to the K-junction 24. When configured in this manner, the electrical field generator 20 can, for example, be used to generate an electrical field at the K-junction 24 when the electrical field generator 20 is connected to a power supply, as further described below.

The ports (e.g., ports 26, 28, 36, 42, 50, 60, 68) can, for example, be connected to the respective channels (e.g., channels 12, 14, 16, 18, 56, 58) by at least one opening in the ports. For example, the first port 26 has an opening 80 which connects the first port 26 to the first end 30 of the main channel 12, as best shown in FIG. 1B. The ports can include various shapes and sizes. The ports can, for example, be generally cylindrical in shape.

The microfluidic device 10 can be formed using photolithography, as will be appreciated by one of ordinary skill in the art. For example, SU8-2025 photoresist can be spin coated onto silicon wafers to create a master mold. Photolithography can then be conducted by placing a photomask with the desired dimensions of the microfluidic device 10 over the photoresist and exposing the mold to an ultraviolet source, followed by development with PGMEA. The master can be surface treated for 4 to 24 hours with (tridecafluoro-1,1,2,2-tetrahydrooctyl) trichlorosilane under vacuum to increase the ease of removing the PDMS device from the master. The PDMS device can be assembled by mixing RTV615A and RTV615B and degassing under vacuum. After curing (e.g., at 65° C. for 1 hour), the PDMS device can be cut out and inlet holes can be perforated with needles. The PDMS device and a glass slide can be cleaned and plasma treated to irreversibly bond the PDMS device to glass, thus forming the microfluidic device 10. The microfluidic device 10 can be pre-treated with 1% by volume (tridecafluoro-1,1,2,2-tetrahydrooctyl)trichlorosilane in Fluoroinert FC-40 carrier fluid to increase channel hydrophobicity.

When the microfluidic device is configured in this manner, the main channel 12, and channels 14, 16, 18 can all be in fluidic communication with each other. For example, a fluid can flow from the first port 26 into and through the main channel 12 and out of the second port 28, or vice versa.

It should be noted that fluid can be injected and/or extracted from any of the ports and/or that fluid can flow in any direction within the channels. It should also be noted that multiple fluid types (e.g., aqueous and/or oil) can flow within the various channels and that multiple fluid types can flow within each channel simultaneously and/or sequentially.

Further, when configured in this manner, the K-junction 24 of the microfluidic device 10 can, for example, be used to generate and/or manipulate droplets. In some particular embodiments, the K-junction 24 can be used for example to inject volume into the droplets, extract volume from the droplets, generate or form droplets, split the droplets, and/or alter droplet spacing.

For example, FIGS. 2A-6D show the microfluidic device 10 being used for multiple fluidic manipulations. Although not shown, to perform the fluidic manipulations, the microfluidic device 10 can, for example, be configured with various fluid supply devices and control mechanisms. For example, fluids can be delivered into the microfluidic device using tubing (e.g., 30 AWG PTFE) which can be injected into the ports from a vial pressurized with compressed gas (e.g., $N_2$). Pressure delivery to the vials can, for example, be controlled by solenoid valves. The solenoid valves can be actuated by a multifunction data acquisition device controlled by software (e.g., LabView). In lieu of or in addition to pressurized vials, one or more pumps can be controllable to vary the rate of flow of fluid in the channels. Suitable pumps can include, for example, syringe pumps.

In each of the examples shown in FIGS. 2A-6D, the microfluidic device 10 is configured such that the main channel 12 and the channels 14, 16 each have a height of about 40 μm and width of about 40 μm. The second side channel 18 has a height of about 40 μm and width of about 25 μm. The opening 54 from the first and second channels 16, 18 into the main channel 12 has a height of about 40 μm and width of about 10 μm. The K-junction 24 is configured such that the angle θ is about 90 degrees, and the angles ϕ and α are each about 45 degrees.

The electric field generator 20 can be configured such an electric field can be generated at the K-junction 24 by providing an electrolytic solution 128 (e.g., 0.5 M NaCl) connected to AC power supply in the source channel 56 and to a ground in the ground channel 58. The electric field is not present in FIGS. 4A-6D. Various other parameters are further described below.

In some embodiment in which a second aqueous fluid 108 flows from the first side channel 16 to the second side channel 18, the second aqueous fluid 108 can, for example, be used as an electrode for droplet manipulations. This can be accomplished, for example, by inserting a wire (e.g., formed from platinum) connected to an electric field source into the pressurized solution vial. The second aqueous fluid 108 can act as a ground. In this configuration the electric field source channel 56 can be used as described above, but the ground channel 58 can be removed because the second aqueous fluid 108 can replace the ground channel 58.

Figure 2A:
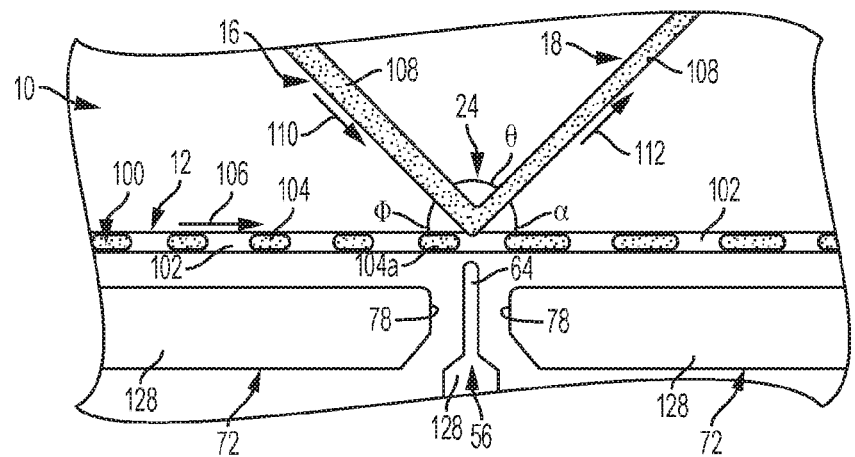
FIGS. 2A-6D show the microfluidic device performing various exemplary functions.
Figure 2B:
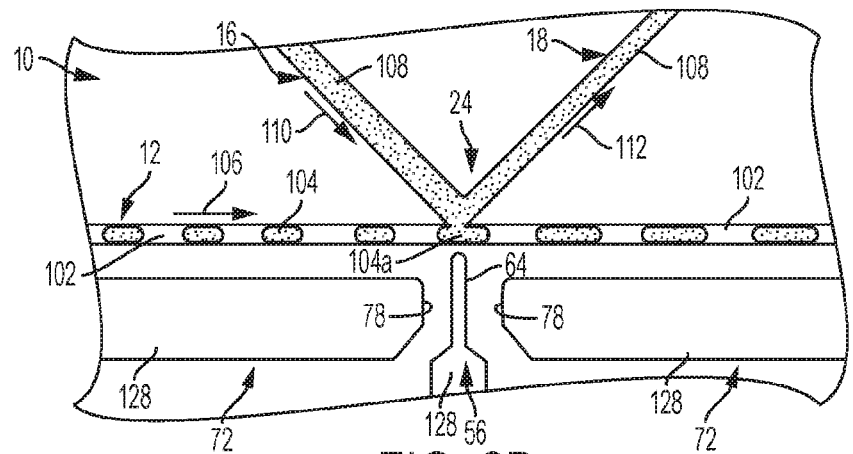
Figure 2C:
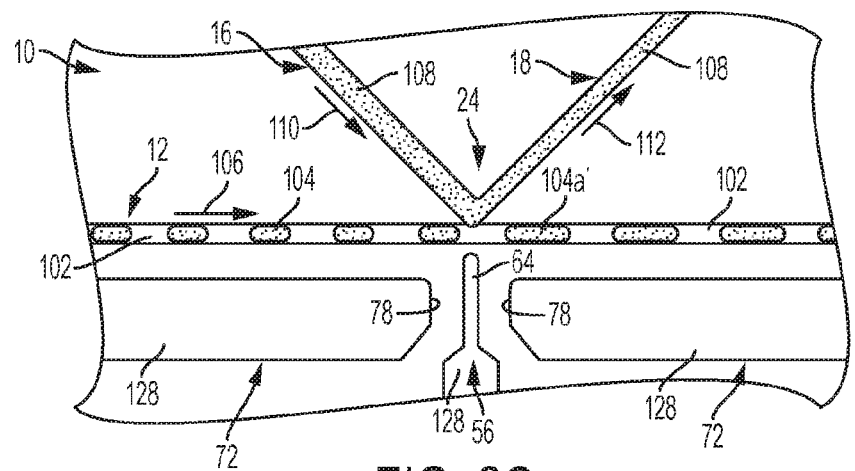

FIGS. 2A-2C show the microfluidic device 10 using a first aqueous fluid 100 and an oil 102 (e.g., 3M® Novec® 7500 Engineered Fluid with 2% by weight poly(ethylene glycol) di-(krytox-FSH amide) added as a surfactant to stabilize droplets) to generate a plurality of aqueous droplets 104. It should be noted that various other oils and surfactants can be used.

Although not shown, the aqueous droplets 104 can, for example, be formed by injecting the oil 102 into the first port 26 and flowing the oil 102 through the main channel 12 at a pressure of 65 kPa towards the second port 28 (i.e., in the direction shown by arrow 106 (FIG. 2A)) and by injecting the first aqueous fluid 100 into the third port 36 and flowing the first aqueous fluid 100 through the droplet formation channel 14 towards the T-junction 22 at a pressure of 60 kPa. In some embodiments, various other pressures (e.g., 0 kPa to 100 kPa) can be used to operate the device. In other embodiments, pressures can exceed 100 kPa (e.g., 150 kPa).

At the T-junction 22, the microfluidic device 10 forms the aqueous droplets 104 separated by the oil 102. Due to the pressure in the main channel 12, the formed aqueous droplets flow from the T-junction toward the K-junction 24.

As shown, the K-junction 24 can, for example, be configured such that a second aqueous fluid 108 flows into the fourth port 42, through the first side channel 16 (i.e., in the direction shown by arrow 110) toward the K-junction 24, and through the second side channel 18 towards the fifth port 50 (i.e., in the direction shown by arrow 112) at a pressure of 45 kPa. Generally speaking, the second aqueous fluid 108 is flowing generally parallel to the flow of the main channel 12. In some embodiments, various other pressures (e.g., 0 kPa to 100 kPa) can be used to operate the device. In other embodiments, pressures can exceed 100 kPa (e.g., 150 kPa).

When configured in this manner, the K-junction 24 can inject or add volume to the droplets 104 as the droplets 104 pass by the K-junction 24. For example, FIG. 2A shows a particular droplet 104a approaching the K-junction 24. FIG. 2B shows the droplet 104a at the K-junction. At this point, the droplet 104a increases its volume by receiving a portion of the second aqueous fluid 108 through the opening 54. Thus, the droplet 104a becomes droplet 104a', 104a' being the droplet 104a formed from the first aqueous fluid 100 plus the additional volume of second aqueous fluid 108, as best shown in FIG. 2C.

The change in volume from the initially formed droplet (e.g., droplet 104a) to the droplet altered by the second aqueous fluid 108 at the K-junction 24 (e.g., droplet 104a') can be adjusted by altering the pressure in the main channel 12 and opening 54 at the K-junction 24. The change in volume can also be adjusted by altering the dimensions (e.g., the widths) of the first and second side channels 16, 18. This can, for example, advantageously allow a user of the microfluidic device 10 to desirably select the pressures and/or dimensions for the desired output. The pressure in the main channel 12 and/or at the opening 52 can be adjusted by changing the pressures applied to ports 26, 28, 36, 42, and/or 50.

Figure 3A:
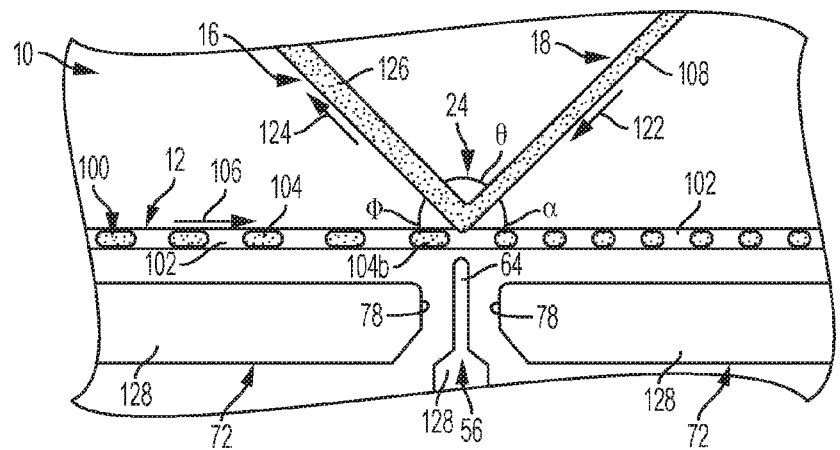
Figure 3B:
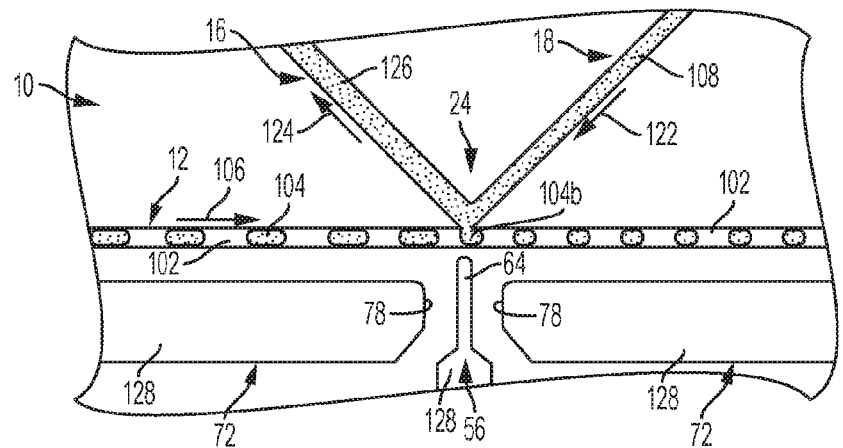
Figure 3C:
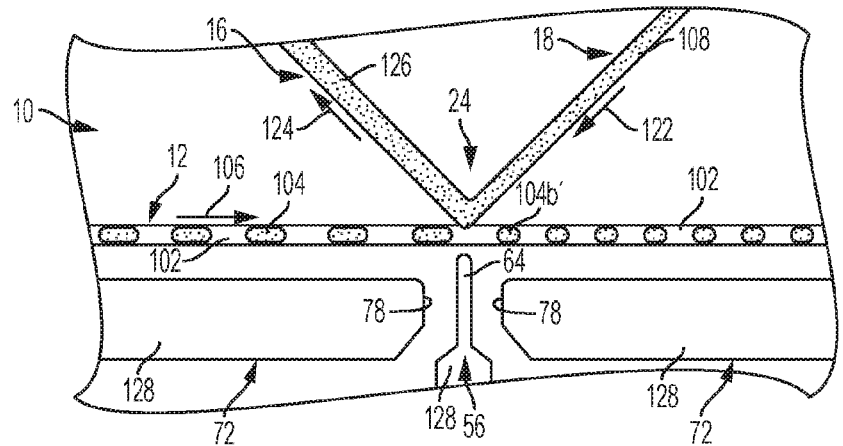

Also, the K-junction can, for example, be used to extract volume from the droplets 104, as shown in FIGS. 3A-3C. In this embodiment, the parameters are the same as in FIGS. 2A-2C except that the second aqueous fluid 108 is flowing in the opposite direction, i.e., the second aqueous fluid 108 is flowing from the fifth port 50, through the second side channel 18 towards the K-junction 24 (i.e., in the direction shown by arrow 122), through the first side channel 16 away from the K-junction 24 (i.e., in the direction shown by arrow 124), towards the fourth port 42. Generally speaking, the second aqueous fluid 108 is flowing generally anti-parallel to the flow of the main channel 12. Also, the pressure at the fifth port 50 has been changed to 20 kPa.

When configured in this manner, the K-junction 24 can extract or remove volume from the droplets 104 as the droplets 104 pass by the K-junction 24. For example, FIG. 3A shows a particular droplet 104b approaching the K-junction 24. FIG. 3B shows the droplet 104b at the K-junction. At this point, the volume of the droplet 104b decreases as a portion of first aqueous fluid 100 is drawn or pulled through the opening 54 into the first side channel 16. Thus, the droplet 104a becomes droplet 104b', 104b' being the droplet 104a formed from the first aqueous fluid 100 minus the volume extracted at the K-junction 24, as best shown in FIG. 3C. In addition the second fluid 108 flowing through the first side channel is also altered by the addition of the volume of the first fluid 100 that is extracted from the droplets 104. As such, the second fluid 108 becomes third aqueous fluid 126.

The change in volume from the initially formed droplet (e.g., droplet 104b) to the droplet reduced at the K-junction 24 (e.g., droplet 104b') can be adjusted by altering the pressure in the main channel 12 and opening 54 at the K-junction 24. As noted above, the pressure in the main channel 12 and/or at the opening 52 can be adjusted by changing the pressures applied to ports 26, 28, 36, 42, and/or 50. The change in volume can also be adjusted by altering the dimensions (e.g., the widths) of the first and/or second side channels 16, 18.

Figure 7A:
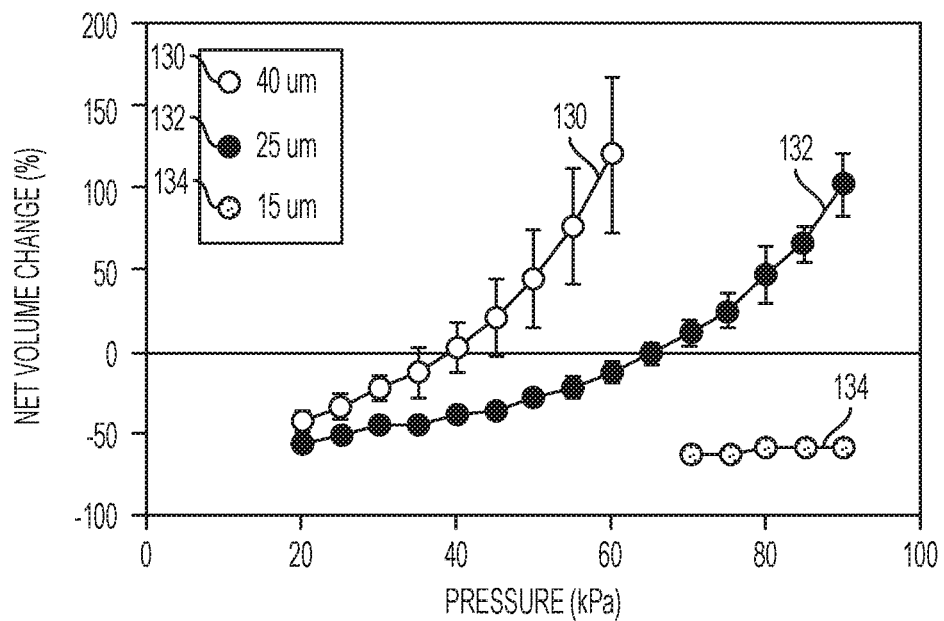
FIGS. 7A-9B are graphs providing data about various embodiments of a microfluidic device.

For example, FIG. 7A shows various percent changes in volume of the droplet for a variety of K-junction pressures (e.g., from about 20 kPa to about 90 kPa), a variety of second side channel 18 widths (i.e., 40 µm, 25 µm, and 15 µm—shown by plot lines 130, 132, 134, respectively), a fixed first side channel 16 width (i.e., 40 µm), and aqueous fluid flow from the second channel 18 to the first side channel 16. To summarize, the overall trend of this configuration is that increasing the width of the second side channel 18 increases the tendency toward injecting fluid into the droplets at the same pressure. Although not shown, the width of the first side channel 16 can also be modified to change performance.

In the illustrated embodiments (e.g., FIGS. 2A-2C), the first aqueous fluid 100 and the second aqueous fluid 108 are the same fluid. In these embodiments, the first aqueous fluid 100 and the second aqueous fluid 108 are mixed to form a third aqueous fluid 126, the third fluid 126 will also be the same.

In alternative embodiments, the first and the second aqueous fluids can, for example, be different fluids. In such embodiments, the third aqueous fluid 126 can comprise a composition which is different than the composition of the first and/or the second aqueous fluids 100, 108.

Figure 4A:
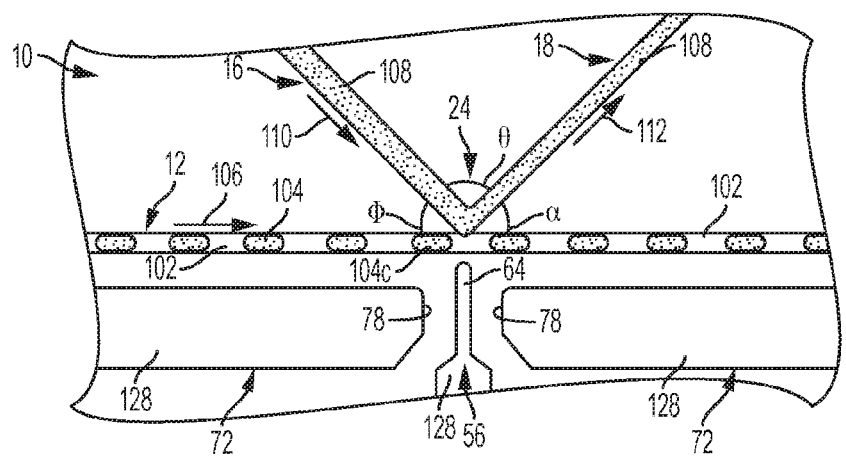
Figure 4B:
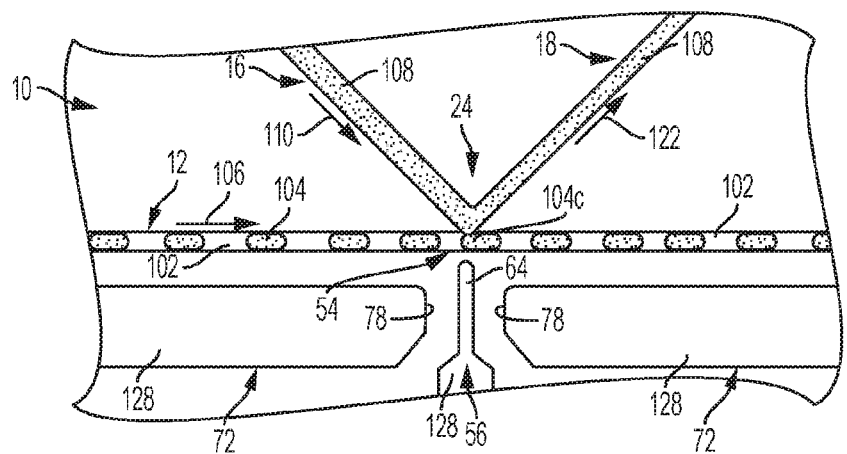
Figure 4C:
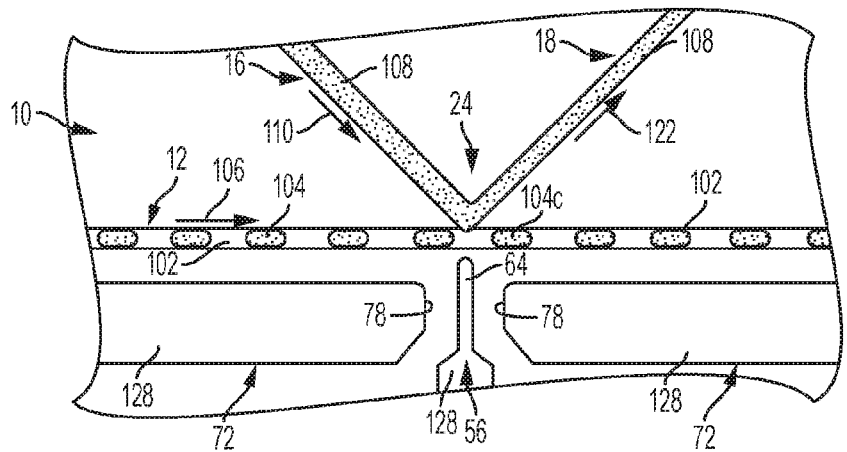

In addition, the K-junction 24 can, for example, be used to balance the second aqueous solution 108 with the passing droplets 104 using parallel flow and/or anti-parallel flow in the absence of an electric field, as shown in FIGS. 4A-4C. In this embodiment, the parameters are the same as in FIGS. 2A-2C, except that the pressure at the opening 54 has been changed to 27 kPa and the electrical field has been removed by turning off the power supply which is connected to the source and ground channels 56, 58. When configured in this manner, the droplets 104 are unaltered as they pass by the K-junction. For example, FIGS. 4A-4C show a particular droplet 104c passing by the K-junction.

Depending on the pressures applied in the balancing configuration, oil 102 can flow through the opening 54 and into the first side channel 16 for antiparallel flow and into the second side channel 18 for parallel flow. This occurs more significantly for lower pressures applied to the fifth port 50 for antiparallel flow and applied to port 42 for parallel flow. When oil 102 flows from the main channel 12 through opening 54 to either the first side channel 16 or the second side channel 18, the spacing between the droplets 104 is reduced.

Further, the K-junction 24 can, for example, be used to form or generate droplets 104 using anti-parallel aqueous fluid 100 flow in the first and second side channels 16, 18 (i.e., flow in the directions shown by arrows 122, 124, respectively). In this particular example, there is an absence of an electric field. As shown, the pressure of the first aqueous solution 100 at the fifth port 50 is about 40 kPa. Oil can, for example, flow through the main channel at 60 kPa in the direction shown by arrow 106.

The K-junction 24 can also be used to form or generate droplets 104 using parallel aqueous fluid 100 flow in the first and second side channels 16, 18 (i.e., flow in the directions shown by arrows 110, 112, respectively (see, e.g., FIG. 2C)).

Figure 5A:
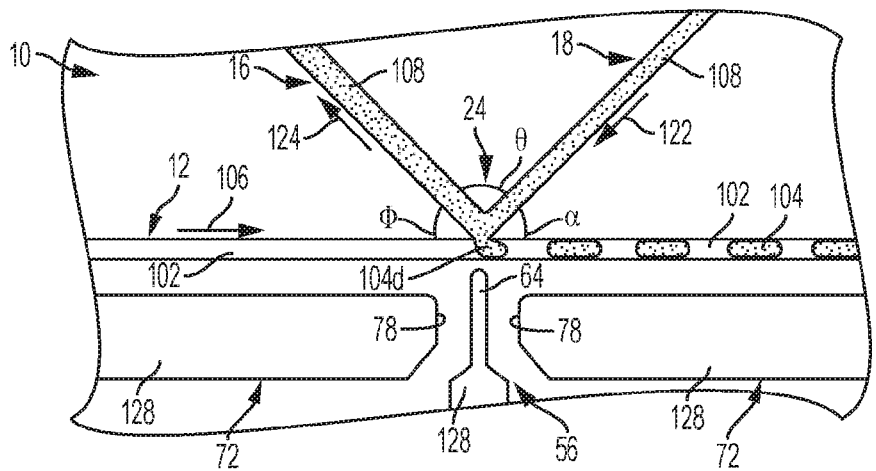
Figure 5B:
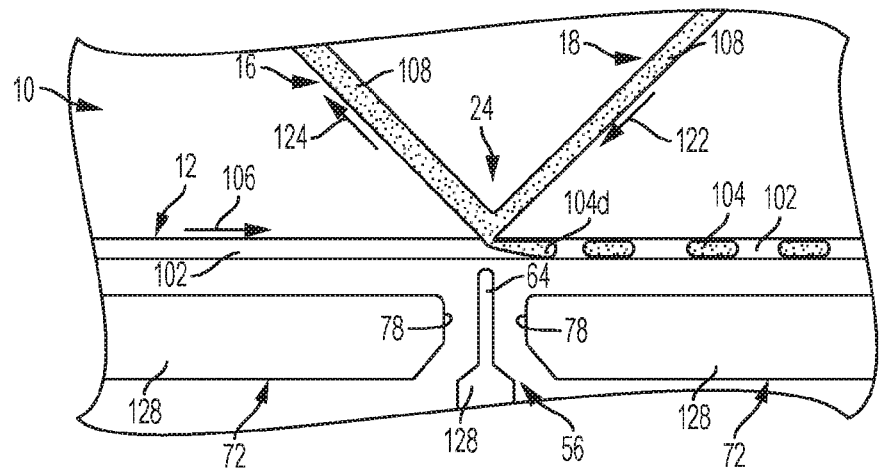
Figure 5C:
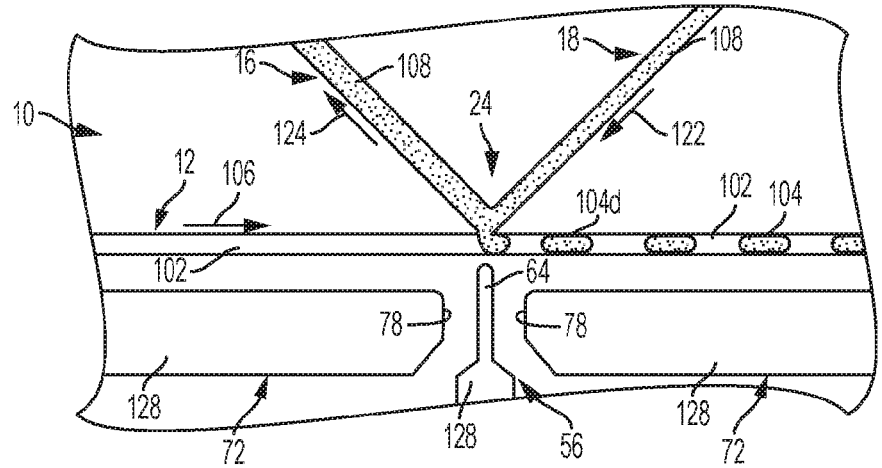

For example, FIG. 5A shows a particular droplet 104d forming at the opening 54 and entering into the main channel 12. FIG. 5B shows the droplet 104d separating from the first aqueous solution 100 and entering the oil 102. FIG. 5C shows the fully formed droplet 104d in the main channel 12.

Figure 14:
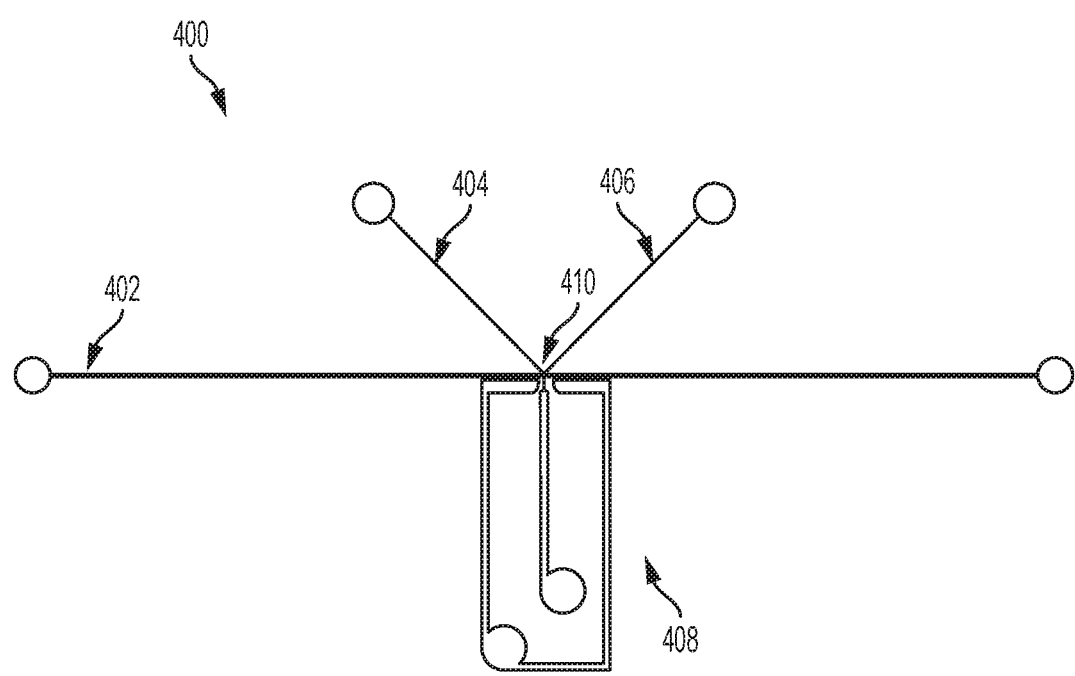
FIG. 14 is a schematic of a microfluidic device, according to another embodiment.

When forming droplets using a K-junction, as described above, a microfluidic device can be configured without a droplet formation channel (e.g., droplet formation channel 14). For example, FIG. 14 show an exemplary embodiment of a microfluidic device 400 which can, for example, be used to generate droplets. In the illustrated embodiment, the microfluidic device 400 is configured in a manner similar to the microfluidic device 10 and includes a main channel 402, a first side channel 404, a second side channel 406, and an electric field generator 408. As shown, the microfluidic device 400 does not have a separate droplet formation channel (e.g., droplet formation channel 14) because the microfluidic device 400 can, for example, use a K-junction 410 (i.e., the junction formed at the intersection of the main channel 402 and the first and second side channels 404, 406) to form the droplets in a manner similar to the K-junction 24 of microfluidic device 10 (e.g., as shown in FIGS. 5A-5C).

In yet another configuration, the K-junction 24 can, for example, be used to split or divide droplets 104 using anti-parallel flow in the absence of an electric field, as shown in FIGS. 6A-6D. The parameters in this configuration are substantially similar to the configuration of FIGS. 3A-3C except that oil 102 rather than aqueous fluid 100 is flowing in an anti-parallel direction through the first and second side channels 16, 18, relative to the main channel 12. The pressure of the oil 102 at the fifth port 50 is 20 kPa.

The K-junction 24 can also be used to split or divide droplets 104 using parallel flow in the absence of an electric field.

Figure 6A:
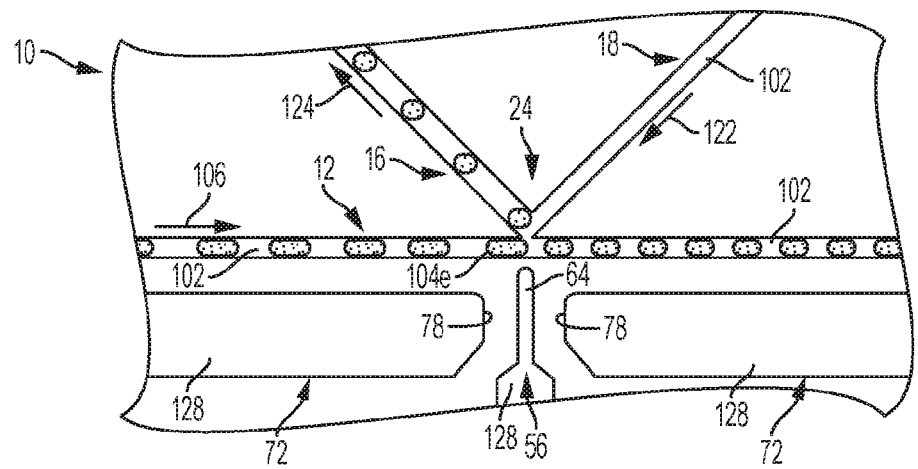
Figure 6B:
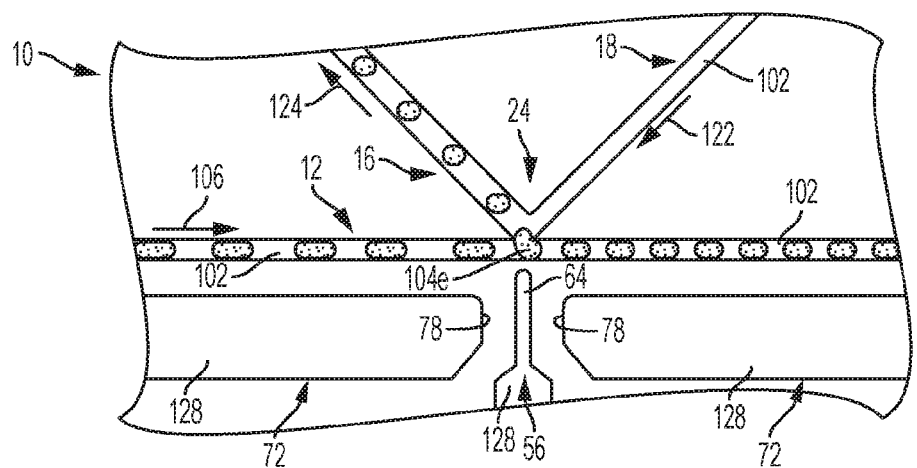
Figure 6C:
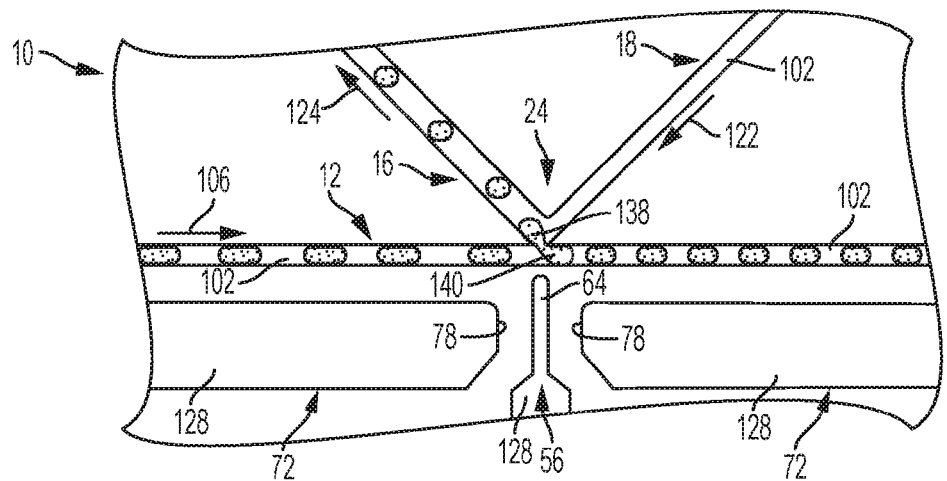
Figure 6D:
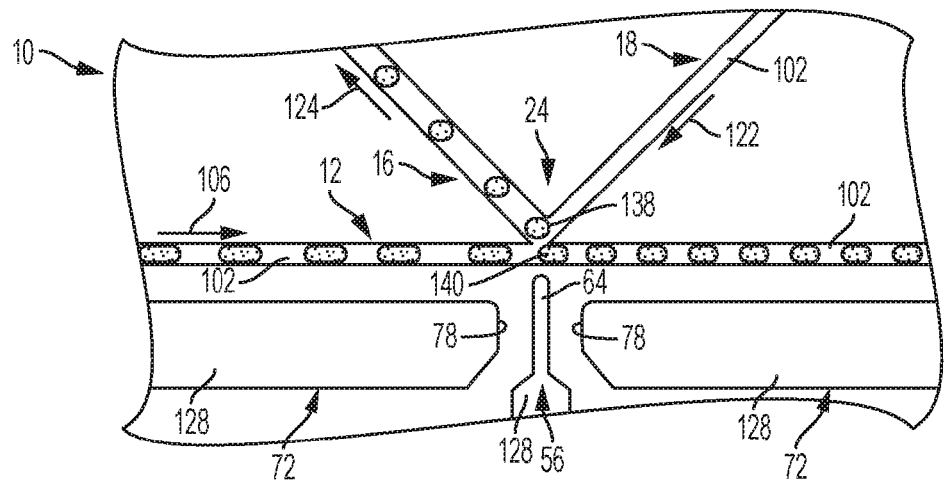

When configured in this manner, the droplets 104 can be formed using the T-junction 22, as described above. As the droplets 104 pass the K-junction 24, the each droplet 104 can be split or divided and a first portion of the each droplet can flow into the first side channel and a second portion can continue to flow through the main channel, as shown in FIG. 6A-6D. For example, FIG. 6A shows a particular droplet 104e approaching the K-junction 24. FIG. 6B shows the droplet 104e at the K-junction as the droplet 104e begins to split. FIG. 6C shows a first portion 138 of the droplet 104e separating from the second portion 140 of the droplet 104e. FIG. 6D shows the first portion 138 of the droplet 104e flowing through the first side channel 16 and the second portion 140 of the droplet 104e flowing through the main channel 12.

Figure 7B:
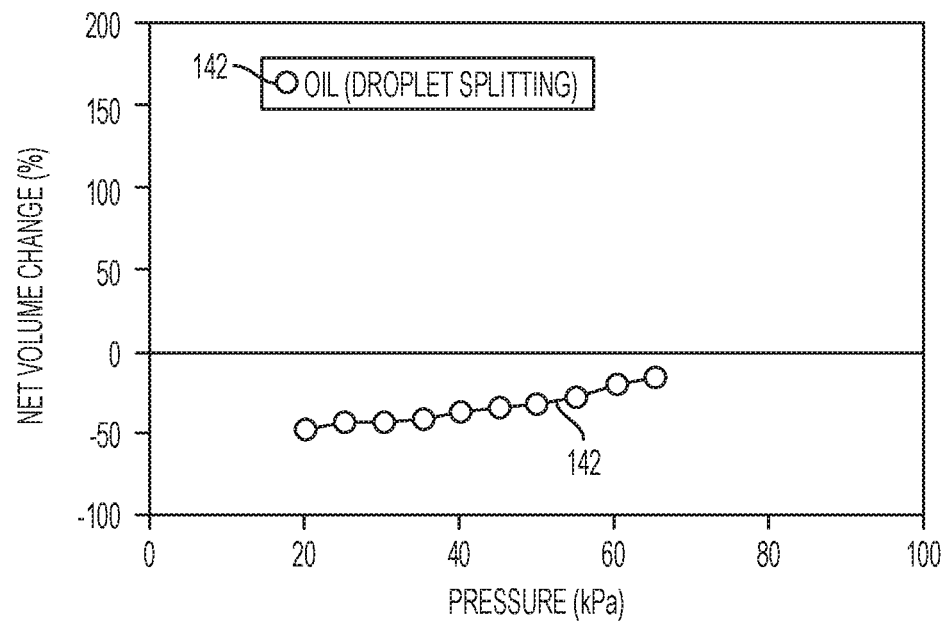

Depending on droplet size and other conditions, droplets may be divided into a first portion which remains in the main channel 12 and one or more secondary portions which are removed (typically through the first side channel 16 for anti-parallel oil flow). For example, FIG. 7B shows a measure of the proportion of droplet volume split off for each applied pressure of anti-parallel flowing oil for the device embodiment in FIG. 1A. The overall trend is that increasing the pressure on the anti-parallel oil flow decreased the proportion of droplet volume split off into the first side channel 16.

The change in volume from the initially formed droplet (e.g., droplet 104e) relative to the second portion of the droplet (e.g., portion 140 of droplet 104e) can be adjusted by altering the pressure in the main channel 12 and opening 54 at the K-junction 24. The change in volume can also be adjusted by altering the dimensions (e.g., the widths) of the first and second side channels 16, 18. For example, FIG. 7B shows a response in net volume change versus the pressure for antiparallel oil applied at the fifth port 50 for a K-junction having a 40 μm wide first side channel 16 and a 25 μm wide second side channel 18. For example, the plot line 142 represents the embodiment shown in FIGS. 6A-6D (i.e., anti-parallel flow in the side channels 16, 18 relative to the main channel 12).

Thus, as shown, the microfluidic device 10 can provide a wide range of functionality in one configuration. This improved functionality and versatility can, for example, allow a single device to perform multiple functions or manipulation on droplets and/or other fluids.

Figure 8A:
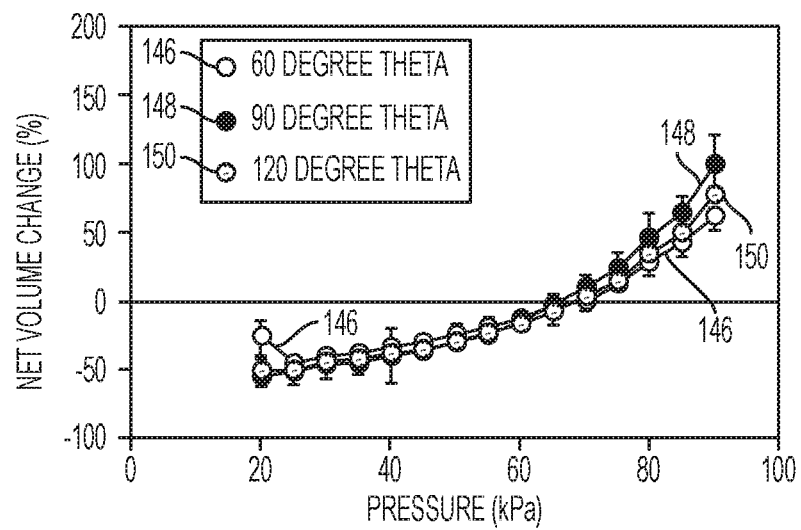

The angles θ, ϕ, α can, for example, also be altered. For example, FIG. 8A shows various volume changes by varying the angle θ from 60 degrees to 120 degrees. For FIG. 8A, the channel dimensions are fixed. Each of the channels has a height of 40 μm, and the main channel 12, the first channel 16, and second channel 18 have widths of 40 μm, 40 μm, and 25 μm, respectively. The opening 54 has height of 40 μm and a width of 10 μm. The K-junction 24 is substantially symmetrical such that as the angle θ is altered, the angles ϕ and α are equally altered. For example, ϕ and α each=(90°−θ/2).

In FIG. 8A, the flow of the droplets in the main channel 12 was in the direction shown by arrow 106 and the flow of the aqueous fluid 100 of the side channels 16, 18 is in the anti-parallel direction shown by the respective arrows 124, 122, similar to the configuration shown in FIG. 3A-3C. The plot lines 146, 148, 150 show that the general trend for this configuration is that altering the angle θ has a relatively minor effect.

Figure 8B:
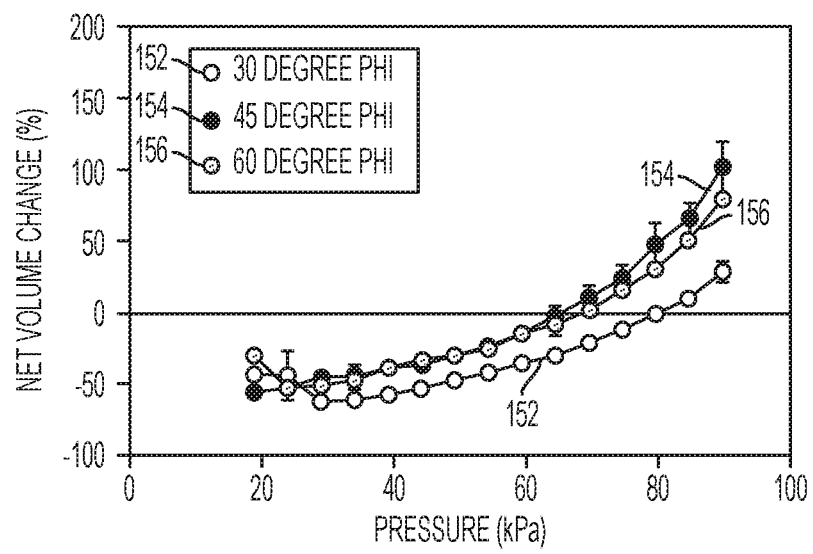

In FIG. 8B, the angle θ is 90 degrees, the angle ϕ varies from 30 degrees to 60 degrees, and the angle α is 90°−ϕ. The other parameters in FIG. 8B are the same as FIG. 8A. The plot lines 152, 154, 156 show that only 30° ϕ (i.e., line 152) varies significantly from the other ϕ values. This is due to the significantly increased volume of the intersection of the first and second side channels at this angle configuration. Because of the increased volume, increased second aqueous fluid flow, derived from increased pressure, must fill the increased volume before performance shifts from extracting to injecting. Therefore, performance shifts to requiring increased pressure.

As shown in FIGS. 8A-8B, manipulating the angles θ, φ, α has relatively little effect on device performance in terms of net volume change effected on the droplets because fluid pressures are exerted uniformly in all directions. Angle variations can, however, change performance if they significantly change the volume of the intersection between the two side channels.

Figure 9A:
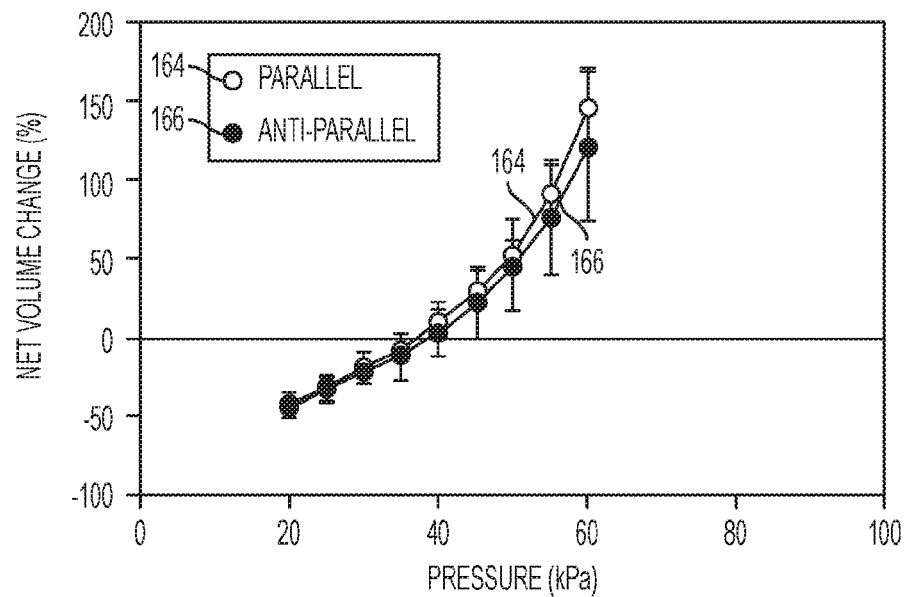

FIG. 9A shows a comparison of net volume change for droplets for parallel (plot line 164) and anti-parallel (plot line 166) aqueous flow behavior versus applied pressure to the second aqueous fluid for a symmetrical K-junction 24. The configuration shown in FIG. 9A has channel heights of 40 μm; channel widths for the main channel, first side channel, and second side channel being 40 μm, 40 μm, and 40 μm, respectively; opening 54 is 10 μm; θ is 90, φ is 45 degrees, α is 45 degrees; oil flow at 65 kPa; and droplet formation at 60 kPa. As shown, changing the flow direction of the side channels 16, 18 has a relatively minor effect on the net volume change performance. This occurs because fluid pressures are applied uniformly in all directions, so net volume change performance should not have a directional dependence on the second aqueous fluid flow. In this example, injections into droplets and extraction from droplets can occur in the presence of an electric field.

Figure 9B:
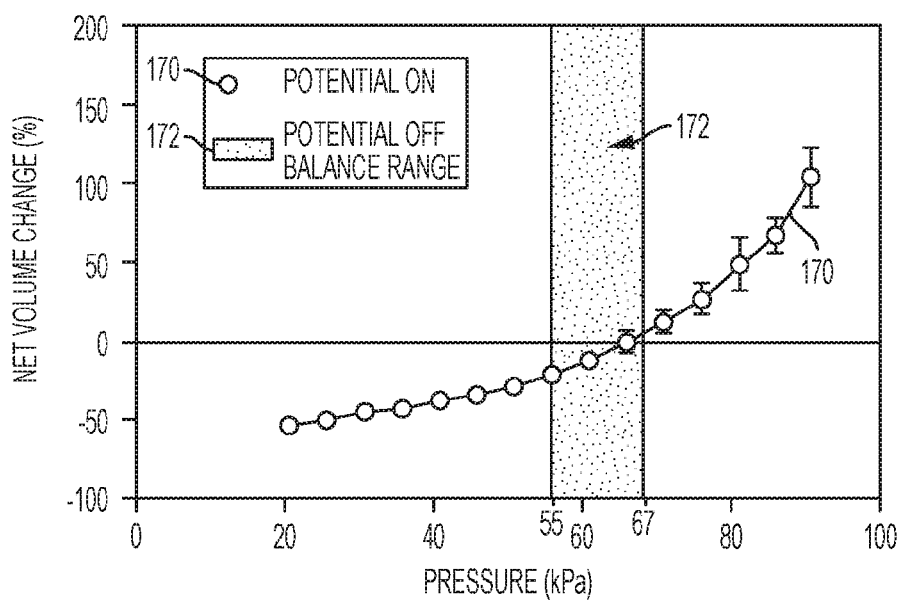

FIG. 9B demonstrates the K-junction's versatility via extraction and injection with an electric potential and balancing behavior without an electric potential for anti-parallel aqueous flow. The configuration shown in FIG. 9B is substantially the same as FIGS. 3A-3C (i.e., channel heights of 40 μm; channel widths for the main channel, first side channel, and second side channel being 40 μm, 40 μm, and 25 μm, respectively; opening 54 is 10 μm; θ is 90, φ is 45 degrees, α is 45 degrees; oil flow at 65 kPa; and droplet formation at 60 kPa). As shown by plot line 170, at low pressures, the device tends to remove volume from droplets, while at high pressures the device tends to inject fluid into droplets in the presence of an electric field. As also shown, the device has a pressure range 172 of about 12 kPa (i.e., from about 55 kPa to about 67 kPa) in which the device performs to balance the interface between the droplets and the second aqueous fluid with the electrical potential off. Thus, the pressure range 172 leaves passing droplets unaltered.

In some embodiments, when the electrical potential is not applied and the pressure is lower than the pressure range 172, droplets from the main channel 12 can split at the K-junction 24 and some of the split droplet material can be lost through the first side channel 16. In some embodiments, when the electrical potential is not applied and the pressure is higher than the pressure range 172, droplets of the second aqueous fluid 108 can form at the opening 54 and enter the main channel 12. Under these conditions (e.g., pressures outside of the pressure range 172) balancing the interface between the droplets and the second aqueous fluid 108 is not achieved, and droplets are altered by the interaction (e.g., size, number, and/or other properties). Throughout the pressure range 172 with the electric potential not applied, in some embodiments, the droplets and second aqueous fluid 108 are balanced at the interface, and the droplets are unaltered. Throughout the pressure range 172 with the electric potential not applied it is still possible for some of the oil in the main channel 12 to exit through the first side channel 16.

For example, in the embodiment shown in FIG. 9B, 0-60% of the oil between the droplets may be removed in the embodiment, thus reducing the spacing between droplets. In this configuration, higher pressures removed less oil.

Figure 15:
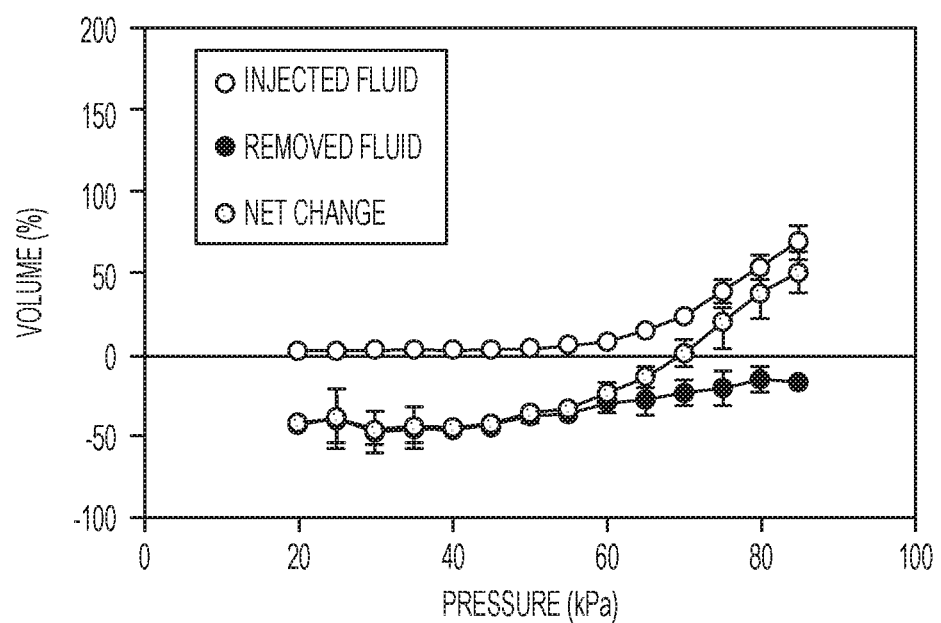
FIG. 15 is a graph providing data about various embodiments of a microfluidic device.

FIG. 15 shows that, in some embodiments, when droplets interact with the second aqueous fluid (from either directional orientation, anti-parallel is shown), a bidirectional exchange of material occurs. As the droplet merges with the second aqueous fluid under the influence of the electric field, droplet aqueous fluid is always mixed into the second aqueous fluid and the second aqueous fluid is always mixed into the droplet. As a result, the net volume change observed for a droplet due to interaction with the second aqueous fluid at the junction is a sum of contributions from the second aqueous fluid injected into the droplet and from droplet material extracted and removed into the second aqueous fluid. For example, negative net volume change indicates more fluid was removed then added, zero net volume change indicates equal removal and addition, and positive net volume change indicates that more fluid was added then removed. FIG. 15 decouples the contributions to indicate for each applied pressure on anti-parallel aqueous second fluid the magnitudes of droplet volume removed, aqueous fluid injected, and net volume change. Overall, pressure increases coincide with larger relative contributions to injection, but at all pressures shown, some fluid is added and some is removed. In this example, the measured pressures (e.g., from about 20 kPa to about 90 kPa) are taken at the fifth port 50.

It should be noted that multiple identical and/or non-identical K-Junction structures can be placed in series along a single main channel to perform combinations of identical and/or non-identical functions. For example, a first K-Junction might remove fluid from a droplet (extraction), while a second K-Junction adds fluid into that droplet (injection).

Figure 10A:
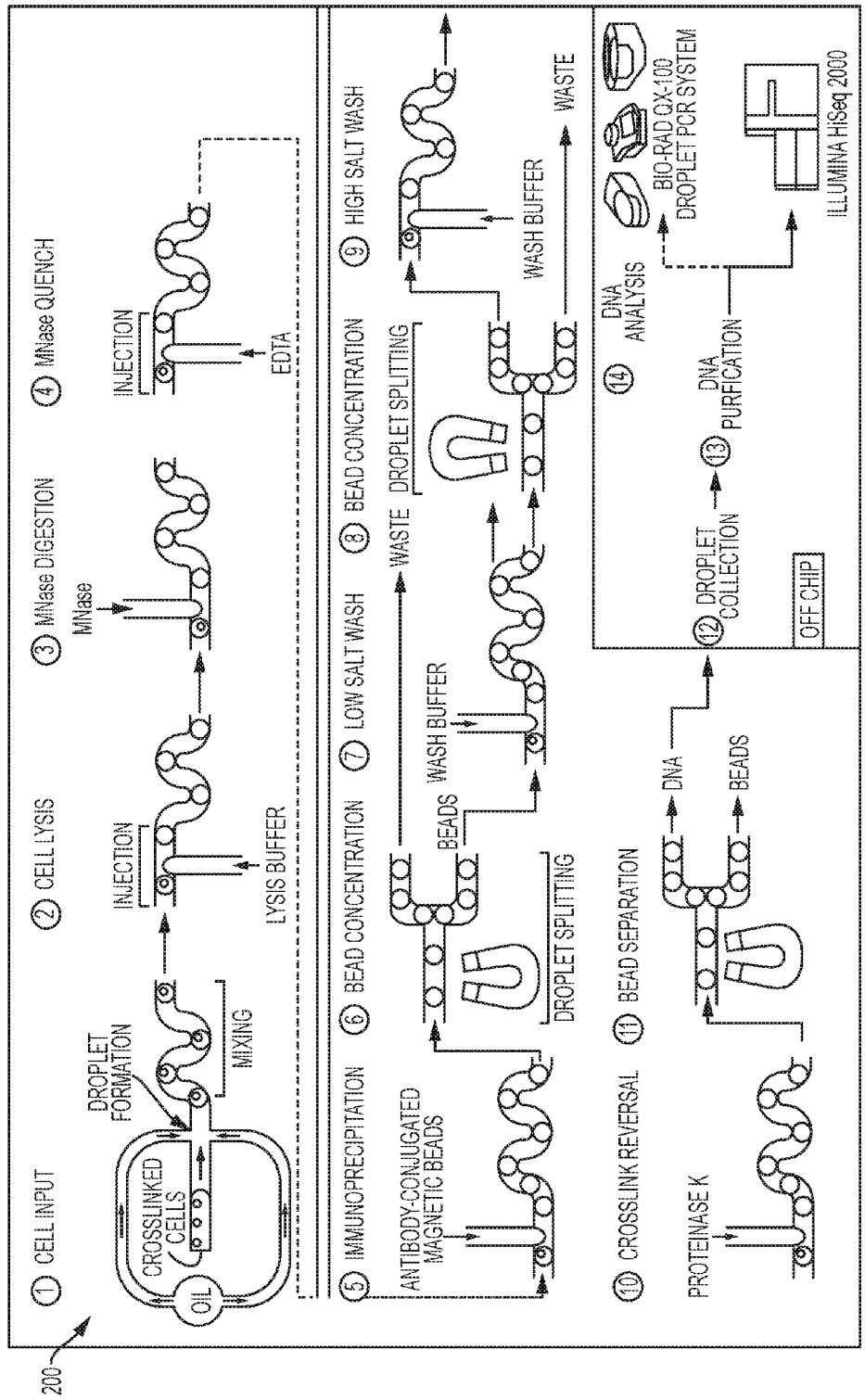
FIGS. 10A-C show various exemplary systems in which the microfluidic device can be used.
Figure 10B:
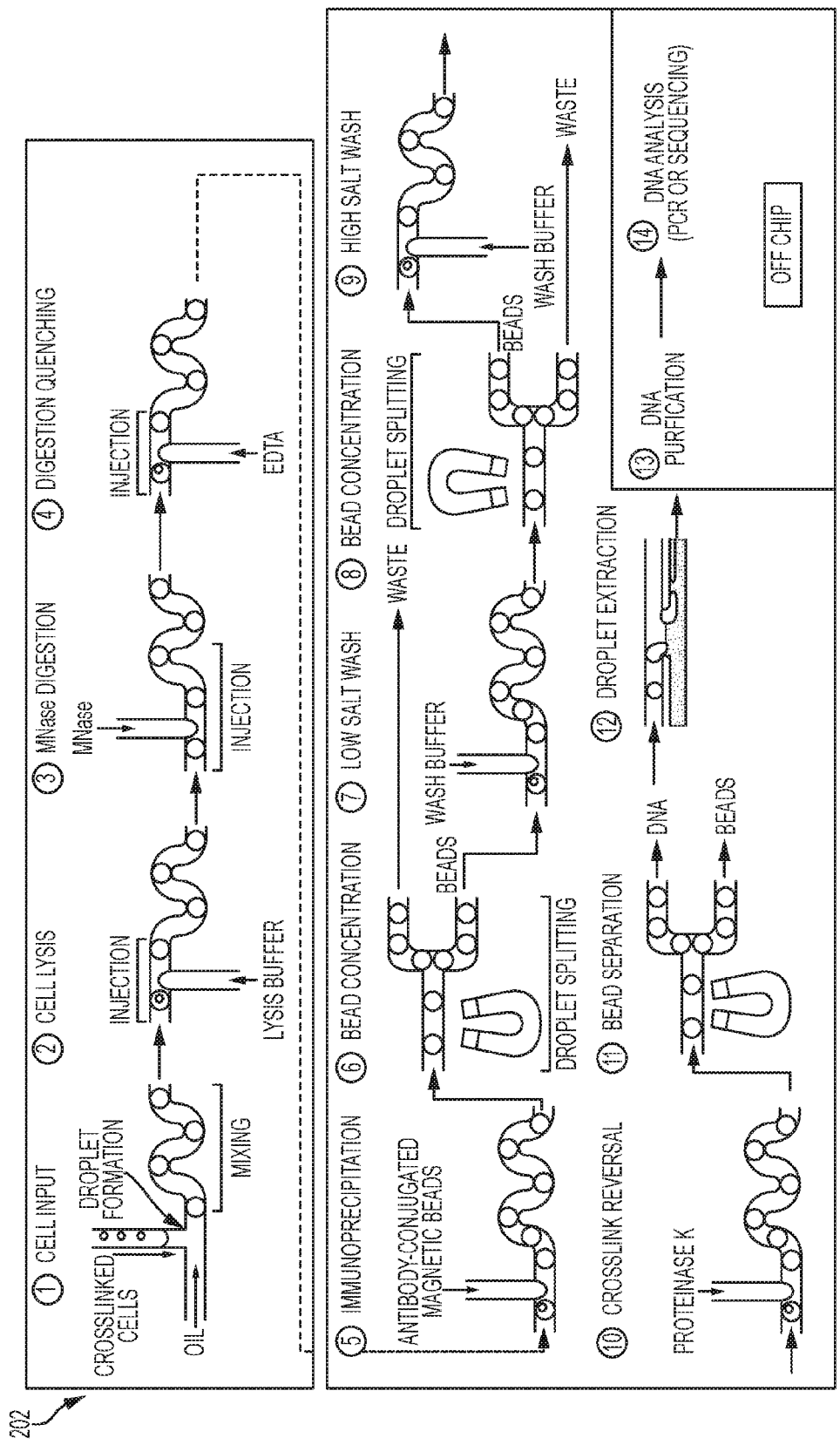
Figure 10C:
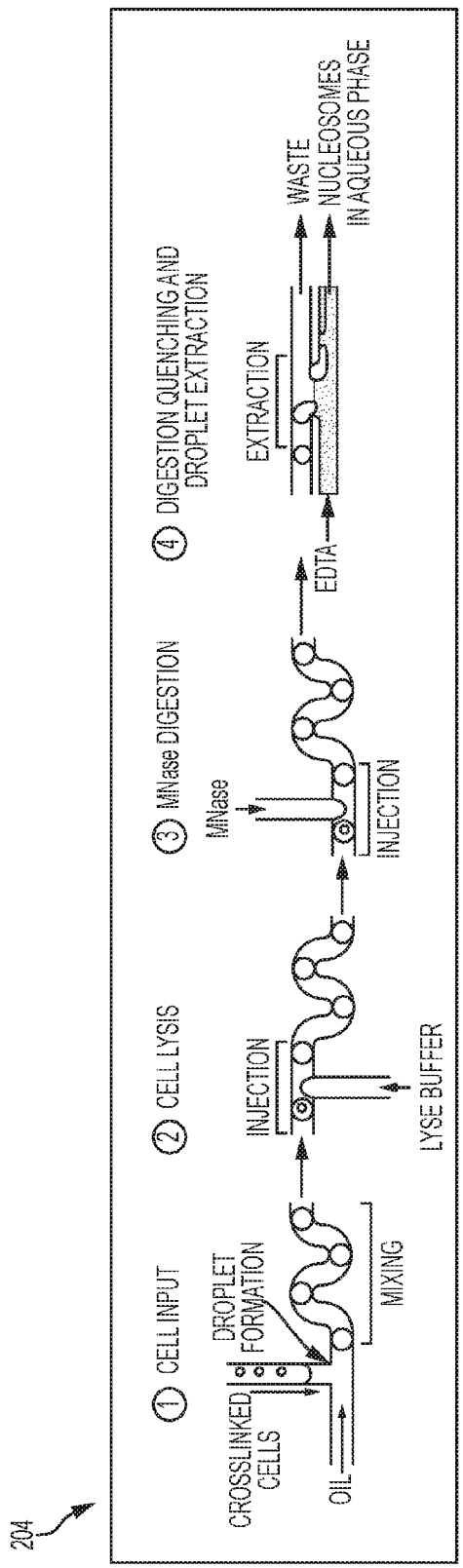

FIGS. 10A-10C shows, for example, a variety of modules or systems 200, 202, 204 that can incorporate the microfluidic device 10. FIG. 10A shows a system 200 for single cell analysis. FIG. 10B shows a system 202 for performing DNA PCR or sequencing. FIG. 10C shows a system 204 for nuclease incubation. In systems 200, 202, 204, the K-junction 24 of the microfluidic device 10 can, for example, be used at the steps (e.g., step 2) where there are T-junctions.

In addition to the systems, 200, 202, 204, the microfluidic device 10 can, for example, be used with a variety of methods comprising the steps shown in FIGS. 10A-10C. In some examples, the disclosed methods allow for high-throughput experimentation, with a small amount of sample. However, one skilled in the art will appreciate that the microfluidic device 10 can, for example, be used in other methods such as other methods that involve detection of a target (which can be qualitative or quantitative), such as a biological target (e.g., nucleic acid molecule, protein, antibody, cell, such a DNA, RNA, antibodies, and the like). For example, the microfluidic device 10 can be used for epigenetic analysis, such as one or more steps of chromatin immunoprecipitation (ChIP) analysis (e.g., see FIGS. 10A-10C), for example to generate nucleosomes or DNA from nucleosomes (in some examples from a single cell or a plurality of cells). In one example, the microfluidic device 10 is used to amplify nucleic acid molecules in the droplet, for example using polymerase chain reaction (PCR) (e.g., in a single droplet, such as a single cell in a single droplet), such as quantitative PCR, real-time PCR, reverse transcriptase PCR, digital droplet PCR, and the like. In one example, the microfluidic device 10 is used for cell sorting, for example to isolate or purify cells or organisms of interest. In one example, the microfluidic device 10 is used to generate a drug delivery system. In one example, the microfluidic device 10 is used to screen test compounds for desired activity. In one example, the microfluidic device 10 is used to crystalize proteins.

FIG. 11A-13C show an example of a microfluidic device 300, according to one embodiment. The device 300 can comprise a main channel portion 302, a droplet formation portion 304, an injector portion 306, a serpentine portion 308, and an extractor portion 310.

The main channel 302 and the droplet formation portion 304 can, for example, be configured to form aqueous droplets 312 (FIGS. 12A-13C), similar to device 10. The injector 306 can, for example, be a K-junction (similar to K-junction 24 of the device 10).

Figure 11A:
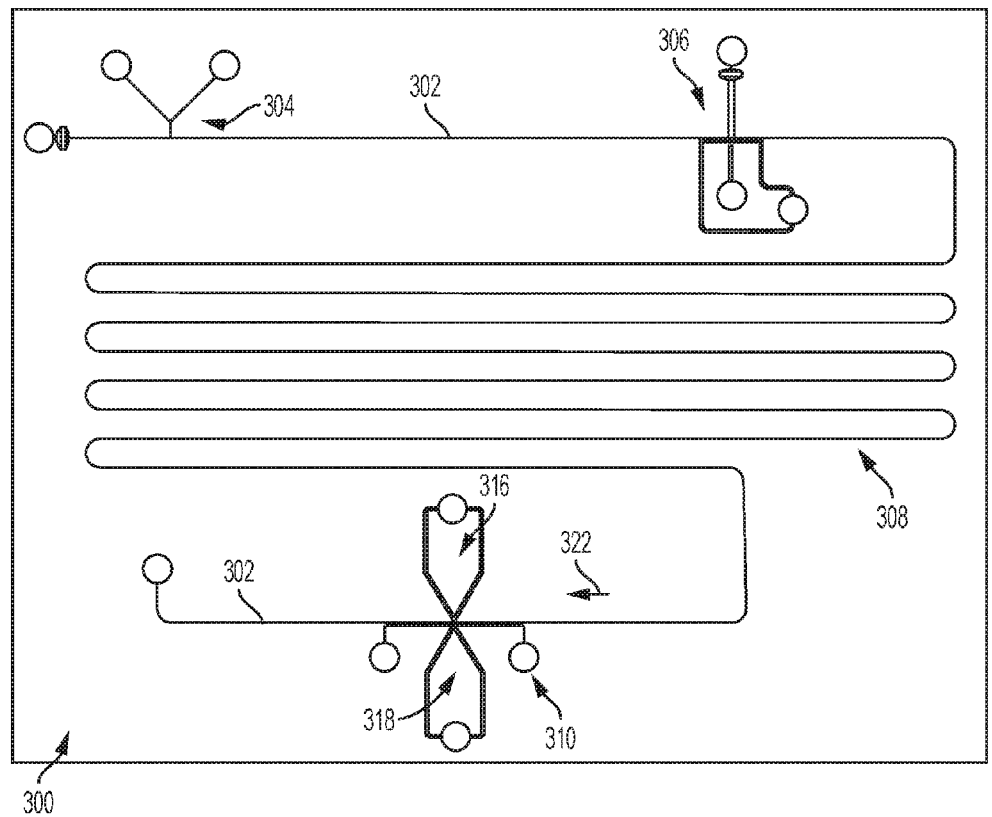
FIG. 11A is a schematic of a microfluidic device, according to another embodiment.
Figure 11B:
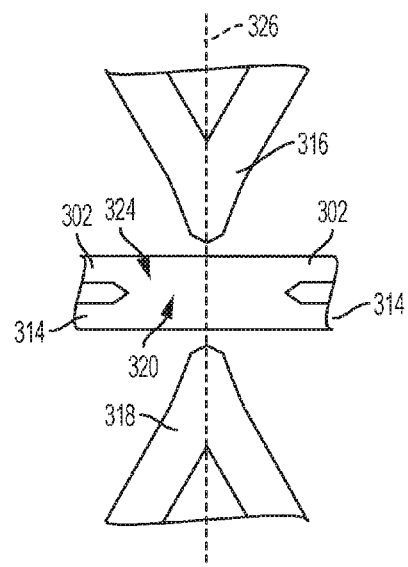
FIG. 11B is a detail view of the microfluidic device of FIG. 11A.

The extractor 310 can, for example, comprise a side channel 314 which is connected to and substantially parallel to the main channel 302 for a portion of the main channel 302 to form a junction 320, as best shown in FIG. 11B. The main channel 302 and the side channel 314 can, for example, be connected via an opening 324 in the main channel 302. The extractor 310 can also include a source channel 316 and a ground channel 318. The source channel 316 and the ground channel 318 can, for example, be used to create an electric field.

The source channel 316 and the ground channel 318 can be arranged such that they are generally opposing one another, and generally aligned with each other in this opposing arrangement, on different sides of the main channel 302. For example, the source channel 316 and the ground channel 318 can be aligned such that the source channel 316 and the ground channel 318 each overlap with an axis which extends through the opening 324 and is substantially perpendicular to the main channel 302 and the side channel 314 at the junction 320. In the illustrated embodiment, for example, the source channel 316 and the ground channel 318 are aligned such that the source channel 316 and the ground channel 318 intersect an axis 326 (FIG. 11B). In the example shown in FIG. 11B, the channels 316, 318 overlap and are generally centered on the axis 326. Aligning the source channel 316 and the ground channel 316 in this manner can, for example, significantly improve the functionality of the extractor 310 when using the extractor 310 to extract droplets from the main channel 302 into the side channel 314, as further described below.

Figure 12A:
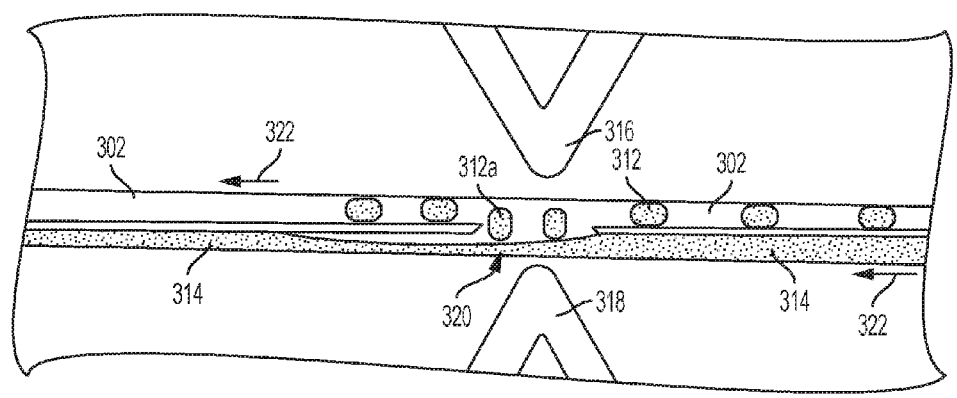
FIGS. 12A-13C show the microfluidic device of FIG. 11A performing various exemplary functions.
Figure 12B:
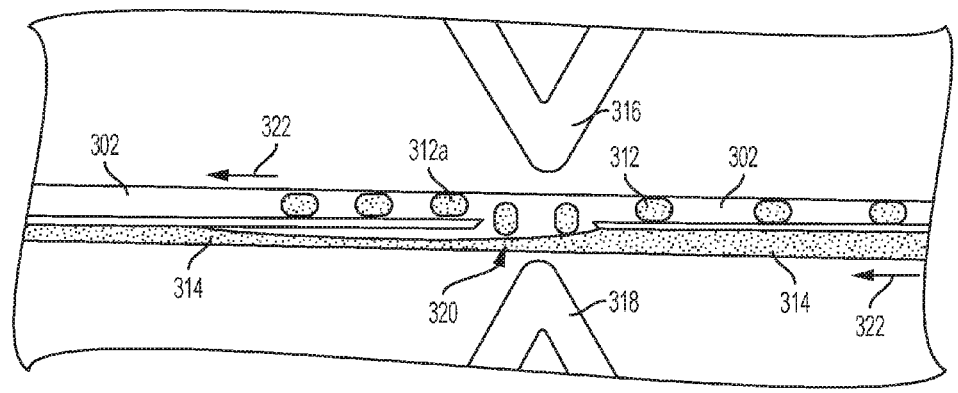
Figure 13A:
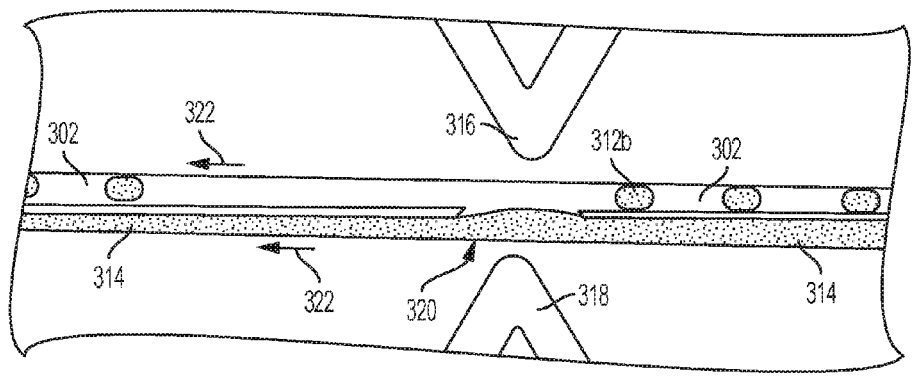
Figure 13B:
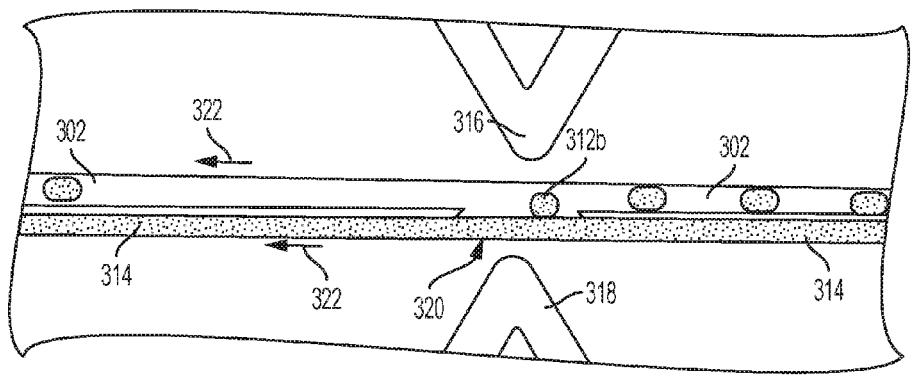
Figure 13C:
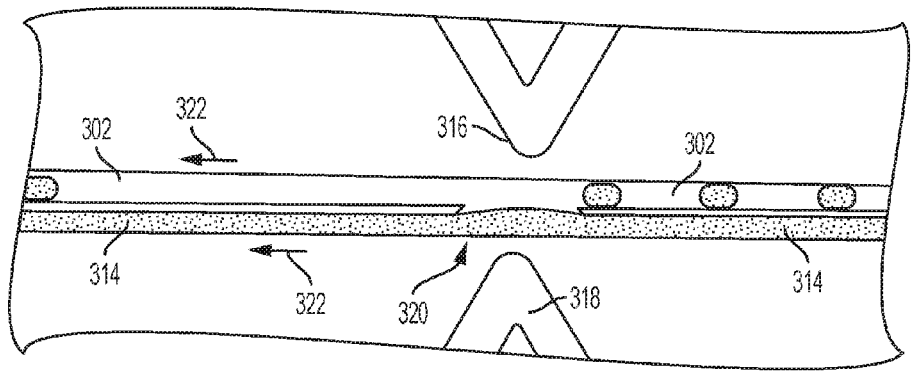

The extractor 310 can, for example, be configured to allow droplets 312 passing through the main channel 302 to remain in the main channel 302 when the source channel 316 is not producing an electrical field or to be pulled or extracted into the side channel 314 of the extractor 310 when the source channel 316 is producing an electrical field. For example, FIGS. 12A-12B show a particular droplet 312a entering the junction 320 flowing in the direction of arrow 322 when the electrical field is not present at the junction 320. As shown in FIG. 12B, the droplet 312a passes over the junction 320 remains in the main channel 302. For example, FIG. 13A-13B shows a particular droplet 312b entering the junction 320 flowing in the direction of arrow 322 when the electrical field is present. As shown in FIG. 13B, the droplet 312a passes over the junction 320 and is extracted into the side channel 314.

FIGS. 16A-18 show an example of a microfluidic device 500, according to another embodiment. The device 500 can, for example, be used for magnetic bead capture. As best shown in FIG. 16A, the device 500 can comprise a PDMS portion 501, a magnet portion 503, and a coverslip portion 505.

The PDMS portion 501 can include a main fluid portion 502 and an electric field portion 504. In one particular embodiment the PDMS portion 501 can be about or less than 20 mm×35 mm×6 mm.

Referring still to FIG. 16A, the fluid portion 502 can comprise a main channel 508, a droplet-formation portion 510, and a K-junction portion 512. The main channel 508 can have an inlet 514 and an outlet 516 disposed at opposite ends of the main channel 508. The droplet-formation portion 510 can include an inlet 518 and a junction 520 that intersects the main channel 508. In some embodiments, the junction 520 can, for example, be a flow focusing junction. The K-junction portion 512 can include first and second side channels 522, 524 having a respective inlet/outlet port 526, 528.

The electric field portion 504 can include an AC electrode 530 and a ground electrode 532. The electrodes 530, 532 can, for example, comprise an electrolytic solution (e.g., 3 M NaCl). The electric field portion 504 can, for example, be used to generate an electric field at or near the K-junction portion 512 of the fluid portion 502.

Figure 16B:
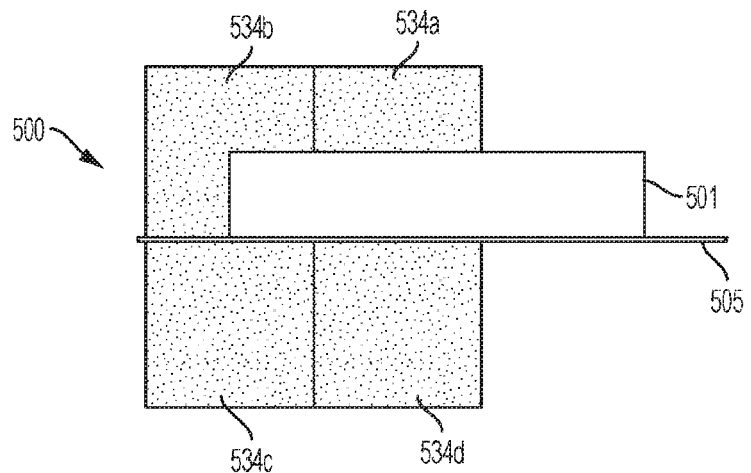
Figure 16C:
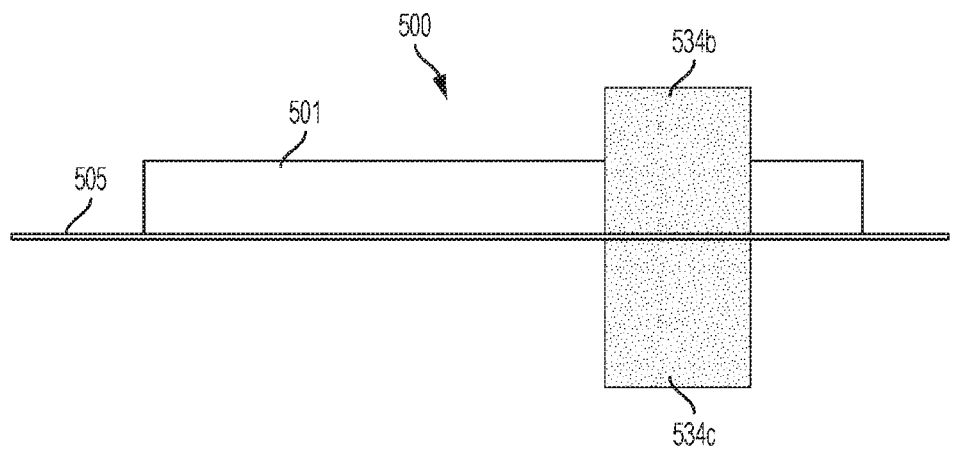

The magnet portion 503 can include one or more magnets (e.g., four in the illustrated embodiment 534a, 534b, 534c, 534d, referred to collectively as "the magnets 534"), as best shown in FIG. 16B. As shown in FIG. 16B-16C, some of the magnets 534 can be disposed above the coverslip (e.g., magnets 534a, 534b), and/or some of the magnets 534 can be disposed below the coverslip (e.g., magnets 534c, 534d). In some embodiments, the magnets 534 can be grade N52 magnets. In one particular embodiment, the magnets 534 are ¼ in.×¼ in.×¼ in. and the magnets 534a, 534d are spaced 250 µm from the K-junction 512 of the PDMS portion 501.

In other embodiments, various other quantities, grades, sizes, spacing, and/or compositions of magnets can be used. For example, the spacing between the magnets and the K-junction can be greater or less than 250 µm and/or there can be fewer or more than four magnets.

The positioning of the magnets relative to the K-junction can also be varied. For example, in some embodiments, the magnets 534 can be laterally aligned with the K-junction 512, as shown in FIG. 16A. In other embodiments, the magnets 534 can, for example, be offset relative to the K-junction 512 (e.g., shifted laterally toward the inlet 514 and/or the outlet 516.

It should be noted that in any of the devices described herein the various ports (e.g., inlet 514, outlet 516) can be an inlet and/or an outlet depending on the direction of fluid flow.

The coverslip portion 505 can, for example, be formed from various materials such as a ceramic (e.g., glass) or polymeric (e.g., polycarbonate) material. In one particular embodiment, the coverslip portion 505 can be about 22 mm×40 mm×0.17 mm.

The device 500 can be used to perform various functions, including generating droplets, extracting/injecting volume from/to droplets, splitting droplets, and/or altering droplet spacing. As noted above, multiple identical and/or non-identical K-junction structures could be placed in series along a single main channel to perform combinations of identical and/or non-identical functions. For example, a first K-junction might remove fluid from a droplet (extraction) while a second K-junction adds fluid into that droplet (injection).

In one particular embodiment, for example, oil is delivered through the inlet 518 of the droplet formation portion 510 at around 65 kPa (e.g., 50-80 kPa). Magnetic bead solution (e.g., containing New England Biolabs Protein A Magnetic Beads or any magnetic microparticle) is delivered though the inlet 514 of the main channel 508 at around 60 kPa (e.g., 0-100 kPa). The magnetic bead solution passes through a turbulent region 536 of the main channel 508.

As best shown in FIG. 16D, the turbulent region 536 of the main channel 508 can have undulating channel walls. The turbulent region 536 can, for example, be used to disperse bead aggregates, which in turn can improve magnetic bead encapsulation reproducibility.

Droplets form at the flow focusing junction 520 where the oil and magnetic bead solution flows intersect. This flow focusing junction 520 is disposed relatively far from the magnet portion 503 in order to minimize the magnetic field present at the magnetic beads which could lead to aggregation and poor magnetic bead encapsulation reproducibility. Droplets travel through the main channel toward the K-junction 512.

At the K-junction various processes can occur (e.g., droplet splitting, volume extraction, etc.) When using the device 500 for droplet splitting, for example, oil flows from the first side channel inlet port 526 through the first side channel 522 toward the K-junction 512 (i.e., parallel flow relative to the main channel 508) at around 10 kPa (e.g., 0-100 kPa). The droplets split at the K-junction based on the applied pressure for the K-junction oil.

The magnet portion 503 pulls magnetic beads away from the K-junction 512 such that droplet material split into the second side channel 524 of the K-junction 512 (e.g., waste droplets) does not contain magnetic beads, while droplet material remaining in the main channel 508 (e.g., sample droplets) does contain magnetic beads.

Sample and waste droplets travel through the main channel 508 and second side channel 524, respectively, to a detection region 538 where magnetic beads can be visualized using microscopy. In some embodiments, visualization is performed here because the close magnet obscures K-junction visualization, the reduced magnetic field of the detection region 538 allows magnetic beads increased circulation throughout the droplets for ease of visibility, and the increased channel width (e.g., 100 um instead of 40 um) of the detection region 538 provides for slower linear velocity that increases the visibility of magnetic beads.

Figure 17A:
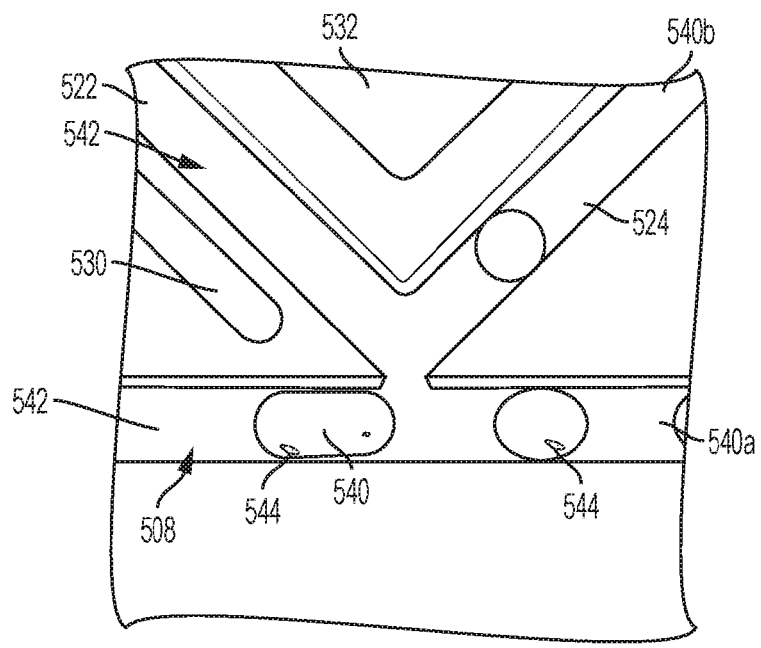
FIGS. 17A-18 show the microfluidic device of FIG. 16A performing various exemplary functions.
Figure 17B:
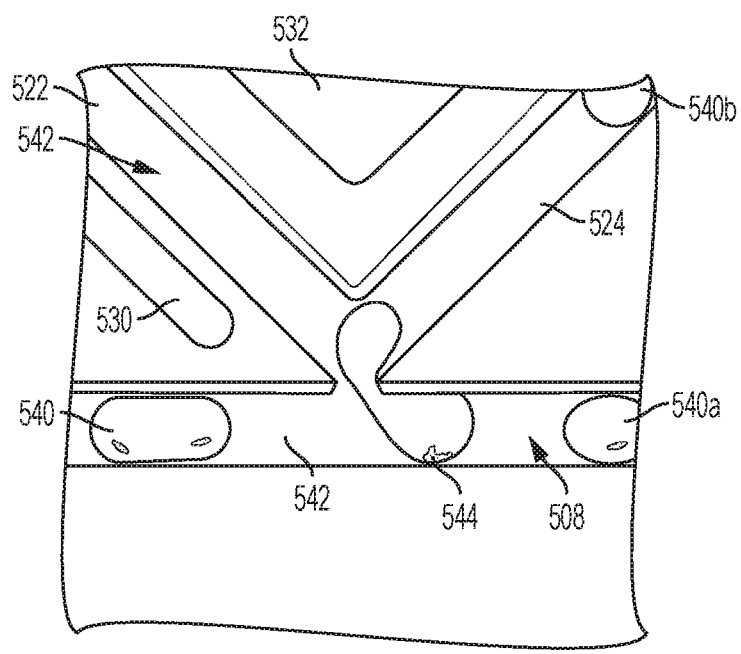
Figure 17C:
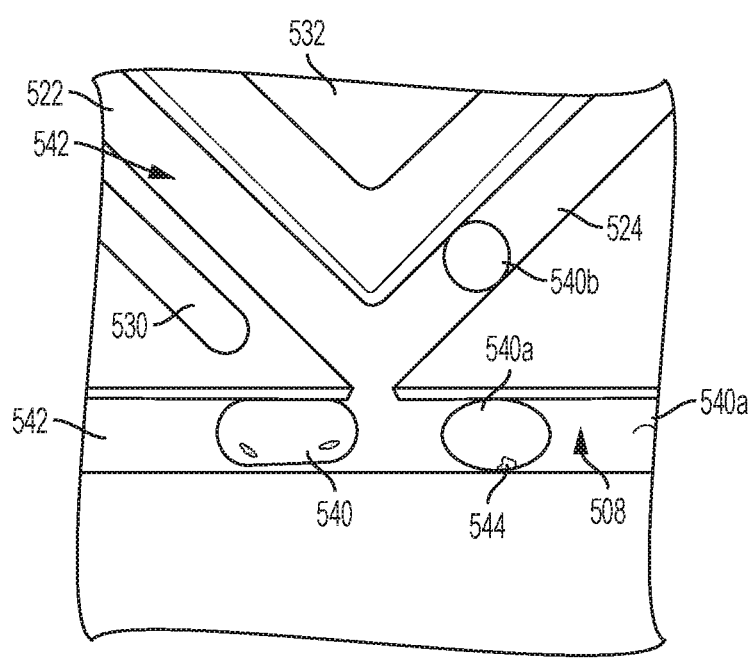

FIGS. 17A-17C show the device 500 being used, for example, to split droplets 540 in oil 542 at the K-junction 512. The droplets 540 are formed via oil 542 at 66 kPa in aqueous bead solution at 63 kPa, and parallel oil flow at 10 kPa (i.e., from the first side channel 522 to the second side channel 524). As shown, due to the magnets 534 (not shown), the droplets 540 split with the magnetic beads 544 (partly visible as dark particles in the droplets 540) remaining in the portion of the droplet 540a in the main channel 508, while the portion of the droplet 540b in the second side channel 524 generally does not comprise magnetic beads 544.

Figure 18:
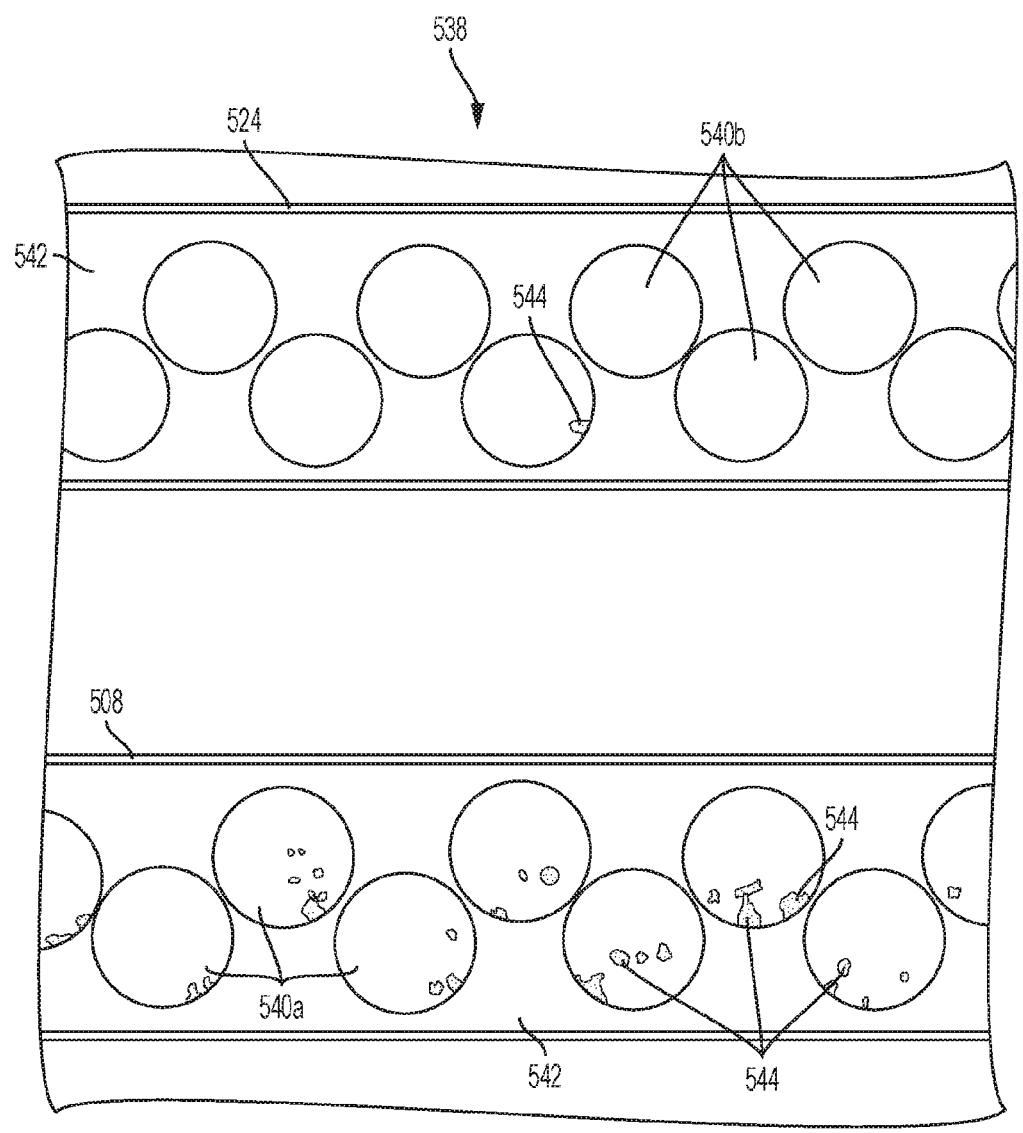

FIG. 18 shows the detection region 538 of the device 500. As shown, the main channel 508 contains droplets 540a with magnetic beads 544. The second side channel 524 contains waste droplets 540b with low incidence of magnetic beads 544. For example, in some embodiments, at least 95% of magnetic beads 544 are retained in the main channel 508, while 48% of droplet volume was split off into the waste droplets 540b in the second side channel 524.

Thus, the device 500 can remove significant droplet volume selectively by not removing magnetic beads in that volume. Magnetic beads may bind sample using common techniques like immunoprecipitation or other methods. Therefore, the device 500 may advantageously remove undesired fluid from a magnetic bead-bound sample, and a desired fluid may then be injected into the droplet using another K-junction on the same device (e.g., in series). Repeating this two-step process exchanges one fluid surrounding a sample for a second fluid, which is a desirable washing process in sample preparation or other chemical processes.

When using the device 500 for volume extraction, for example, washing buffer flows from the first side channel inlet port 526 through the first side channel 522 toward the K-junction 512 (i.e., parallel flow relative to the main channel 508) at around 10 kPa (e.g., 0-100 kPa). The droplets experience volume removal at the K-junction based on the applied pressure for the K-junction washing buffer in the presence of AC electric field delivered by the AC electrode channel 530. The channel is grounded by the ground electrode channel 532.

The magnet portion pulls magnetic beads away from the K-junction such that droplet material removed into the second side channel 524 of the K-junction 512 (e.g., waste flow) does not contain magnetic beads while droplet material remaining in the main channel 508 (e.g., sample droplets) does contain magnetic beads.

Sample droplets and waste flow travel through the main channel 508 and the second side channel 524, respectively, to the detection region 538 where magnetic beads can be visualized using microscopy.

It should be noted that, although examples and/or embodiments of the microfluidic devices described herein are generally directed toward droplet based microfluidics, the microfluidic devices can be used for other applications where control and manipulation of fluids is desirable.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A device comprising:
   a main microchannel defining a main fluid flow path and having a first end portion, a second end portion, a first opening, and a second opening, wherein the first opening is disposed between the first end portion and the second opening, and wherein the second opening is disposed between the first opening and the second end portion;
   a first microchannel defining a first fluid flow path, the first fluid flow path being in fluidic communication with the main fluid flow path via the second opening, the first microchannel forming a first angle relative to the main microchannel, the first angle being less than 90 degrees;
   a second microchannel defining a second fluid flow path, the second fluid flow path being in fluidic communication with the main fluid flow path via the second opening and in fluidic communication with the first fluid flow path, the second microchannel forming a second angle relative to the main microchannel, the second angle being less than 90 degrees, wherein the first and second microchannel form a third angle relative to one another, the third angle being between 60 and 135 degrees;

an electric field generator having one or more microchannels positioned adjacent the main fluid flow path at the location of the second opening; and a third microchannel defining a third fluid flow path, the third fluid flow path being in fluidic communication with the main fluid flow path via the first opening, wherein the main fluid flow path has an oil flowing therein from the first end portion of the main microchannel toward the second end portion of the main microchannel, wherein the main microchannel and the third microchannel are configured for forming one or more aqueous droplets in the oil flow at the first opening of the main microchannel, wherein the aqueous drops flow in the main fluid flow path from the first opening of the main microchannel toward the second end portion of the main microchannel, and wherein the main microchannel, the first and second microchannels, and the electric field generator are configured for manipulating the volume of the aqueous droplets in the oil as the aqueous droplets and the oil pass by the second opening of the main microchannel and continue in the main fluid flow path toward the second end portion of the main microchannel.

2. The device of claim 1, further comprising:
a main fluid control member configured to control the flow of the aqueous droplets and the oil in the main fluid flow path, wherein the oil and the aqueous droplets are a first fluid; and
at least one additional fluid control member configured to control the flow of a second fluid in the first and second fluid flow paths.

3. The device of claim 2, wherein the main fluid control member is configured to cause the first fluid to flow along the main fluid flow path in a first direction, and wherein the additional fluid control member is configured to cause the second fluid to flow along the first and second fluid flow paths in a second direction, wherein at the second opening of the main microchannel, the second direction is generally parallel to the first direction.

4. The device of claim 2, wherein the main fluid control member is configured to cause the first fluid to flow along the main fluid flow path in a first direction, and wherein the additional fluid control member is configured to cause the second fluid to flow along the first and second fluid flow paths in a second direction, wherein at the second opening of the main microchannel, the second direction is generally opposite to the first direction.

5. The device of claim 1, wherein only the first and second microchannels are in fluidic communication with the second opening of the main microchannel, and wherein the main microchannel and the first and second microchannels form a K-junction at the second opening.

6. The device of claim 5, wherein only the third microchannel is in fluidic communication with the first opening of the main microchannel, and wherein the main microchannel and the third microchannel form a T-junction at the first opening.

7. A method for manipulating droplets in a microfluidics system, the method comprising:
delivering a plurality of aqueous droplets and a first fluid along a main fluid flow path of a main microchannel, wherein one or more of the aqueous droplets has a first volume;
delivering a second fluid along a side flow path defined by intersecting first and second microchannels, the first and second microchannels forming an angle therebetween and intersecting with one another at an opening in the main microchannel; and
altering the first volume of the one or more aqueous droplets as respective aqueous droplets move along the main fluid flow path and pass the opening in the main microchannel, wherein after passing the opening, the one or more aqueous droplets continue along the main fluid flow path in the first fluid and have a second volume that is less than or greater than the first volume.

8. The method of claim 7, wherein the act of altering the volume of the one or more aqueous droplets comprises:
removing a portion of the one or more aqueous droplets and directing the removed portion into the side flow path.

9. The method of claim 7, wherein the act of altering the volume of the one or more aqueous droplets comprises:
increasing the volume of the one or more aqueous droplets by injecting a fluid from the side flow path into the main fluid flow path.

10. The method of claim 7, wherein the first fluid is delivered along the main fluid flow path in a first direction and the second fluid is delivered along the side flow path in a second direction, and at the intersection of the first and second microchannels the second direction is generally parallel to the first direction.

11. The method of claim 7, wherein the first fluid is delivered along the main fluid flow path in a first direction and the second fluid is delivered along the side flow path in a second direction, and at the intersection of the first and second microchannels the second direction is generally opposite of the first direction.

12. The method of claim 7, further comprising:
applying an electric field to the aqueous droplets adjacent to the opening in the main microchannel.

13. A method for manipulating droplets in a microfluidics system, the method comprising:
delivering a plurality of droplets and a first fluid along a main fluid flow path of a main microchannel;
delivering a second fluid along a side flow path defined by intersecting first and second microchannels, the first and second microchannels forming an angle therebetween and intersecting with one another at an opening in the main microchannel; and
increasing the volume of one or more of the droplets by injecting a fluid from the side flow path into the main fluid flow path as respective droplets move along the main fluid flow path and pass the opening in the main microchannel.

14. A device comprising:
a main microchannel defining a main fluid flow path and having an opening;
a first microchannel defining a first fluid flow path, the first fluid flow path being in fluidic communication with the main fluid flow path via the opening, the first microchannel forming a first angle relative to the main microchannel, the first angle being less than 90 degrees;
a second microchannel defining a second fluid flow path, the second fluid flow path being in fluidic communication with the main fluid flow path via the opening and in fluidic communication with the first fluid flow path, the second microchannel forming a second angle relative to the main microchannel, the second angle being less than 90 degrees, wherein the first and second microchannels form a third angle relative to one another, the third angle being between 60 and 135 degrees; and an electric field generator having one or more microchannels positioned adjacent the main fluid flow path at the location of the opening, wherein the opening of the main microchannel is a second opening, and the main microchannel further comprises a first end portion, a second end portion, and a first opening, wherein the first opening is disposed between the first end portion and the second opening and is configured to form one or more water-in-oil droplets in the main fluid flow path, and wherein the second opening is disposed between the first opening and the second end portion and is configured for manipulating the one or more water-in-oil droplets.

15. The device of claim 14, further comprising:
a main fluid control member configured to control the flow of the one or more water-in-oil droplets in the main fluid flow path, wherein the one or more water-in-oil droplets are a first fluid; and
at least one additional fluid control member configured to control the flow of a second fluid in the first and second fluid flow paths.

16. The device of claim 15, wherein the main fluid control member pressurizes the first fluid to a first pressure, and wherein the additional fluid control member pressurizes the second fluid to a second pressure that is less than the first pressure.

17. The device of claim 16, wherein the first microchannel has a first width, and the second microchannel has a second width, and wherein the first and second widths are at least substantially equal to each other.

18. The device of claim 15, wherein the main fluid control member pressurizes the first fluid to a first pressure, and wherein the additional fluid control member pressurizes the second fluid to a second pressure that is greater than the first pressure.

19. The device of claim 18, wherein the first microchannel has a first width, and the second microchannel has a second width, and wherein the second width is less than the first width.

* * * * *